(12) United States Patent
Feng et al.

(10) Patent No.: US 8,853,367 B1
(45) Date of Patent: Oct. 7, 2014

(54) COMPOSITIONS AND METHODS FOR MODULATING RANK ACTIVITIES

(75) Inventors: Xu Feng, Birmingham, AL (US); Wei Liu, Shenzhen (CN); Duorong Xu, Guangzhou (CN)

(73) Assignee: The UAB Research Foundation, Birmingham, AL (US)

(*) Notice: Subject to any disclaimer, the term of this patent is extended or adjusted under 35 U.S.C. 154(b) by 1873 days.

(21) Appl. No.: 11/662,799

(22) PCT Filed: Sep. 14, 2005

(86) PCT No.: PCT/US2005/032396
§ 371 (c)(1),
(2), (4) Date: Sep. 21, 2007

(87) PCT Pub. No.: WO2006/031718
PCT Pub. Date: Mar. 23, 2006

Related U.S. Application Data

(60) Provisional application No. 60/609,822, filed on Sep. 15, 2004.

(51) Int. Cl.
*C12P 21/08* (2006.01)
*A61K 38/00* (2006.01)
*C07K 1/00* (2006.01)
*C12P 21/04* (2006.01)

(52) U.S. Cl.
USPC ........ 530/387.3; 530/300; 530/350; 435/69.7

(58) Field of Classification Search
None
See application file for complete search history.

(56) References Cited

U.S. PATENT DOCUMENTS 6,271,349 B1    8/2001   Dougall et al.

FOREIGN PATENT DOCUMENTS

WO    WO 96/06188    *    2/1996
WO    WO 02/24896 A2    3/2002

OTHER PUBLICATIONS

Rothe et al. The TNFR2-TRAF Signaling Complex Contains Two Novel Proteins Related to Baculoviral Inhibitor of Apoptosis Proteins. Dec. 29, 1995. Cell. vol. 83, p. 1243-1252.*
Liu et al. Functional Identification of Three Receptor Activator of NF-κB Cytoplasmic Motifs Mediating Osteoclast Differentiation and Function. Dec. 24, 2004. The Journal of Biological Chemistry. vol. 279, No. 52. pp. 54759-54769.*
International Search Report for PCT/US2005/032396 Dated Aug. 16, 2006. 2 pages.

* cited by examiner

*Primary Examiner* — Anne Gussow
*Assistant Examiner* — Channing S Mahatan
(74) *Attorney, Agent, or Firm* — Sutherland Asbill & Brennan LLP

(57) ABSTRACT

The present invention provides methods for identifying agents capable of modulating RANK-mediated signaling pathways. The present invention also provides compositions and methods of using the same to treat osteoporosis or other RANK-related diseases. The present invention is based on the functional and structural analysis of three TRAF-binding motifs (PTM)—namely, PTM3, PTM5, and PTM6, each of which has been found to play a distinct role in the activation of RANK-mediated intracellular signaling. These PTMs can be used to screen for RANK modulators. These PTMs also represent potential drug targets for diseases that are associated with abnormal RANK expression or activity.

14 Claims, 21 Drawing Sheets

A

B

A

B

C

D

COMPOSITIONS AND METHODS FOR MODULATING RANK ACTIVITIES

This application is a national stage application under 35 U.S.C. §371 from International Application No. PCT/US2005/032396, filed Sep. 14, 2005, which claims priority benefit of U.S. Provisional Application No. 60/609,822, filed Sep. 14, 2004, the entire disclosures of which are incorporated herein by reference.

GOVERNMENT INTERESTS

This invention was made at least in part by using funds from National Institutes of Health Grant AR 47830 (X.F.), National Institutes of Health RCC Grant "UAB Core Center for Musculoskeletal Disorders (P30AR46031)." Consequently, the federal government may have certain rights in this invention.

SEQUENCE LISTING

The instant application contains a Sequence Listing which has been submitted in ASCII format via EFS-Web and is hereby incorporated by reference in its entirety. Said ASCII copy, created on Mar. 28, 2012, is named 23976002.txt and is 22,985 bytes in size.

FIELD OF THE INVENTION

The present invention relates to the structure and function of TRAF-binding motifs (PTMs) in the cytoplasmic domain of RANK and methods for identifying. RANK modulators. The present invention also relates to compositions and methods for treating osteoporosis and other RANK-related diseases.

BACKGROUND OF THE INVENTION

Osteoclasts, the principal bone-resorbing cells, play a pivotal role in skeleton development and maintenance. Osteoclasts are derived from mononuclear precursors of monocyte/macrophage lineage upon stimulation of two key factors: monocyte/macrophage colony stimulating factor (M-CSF) and receptor activator of nuclear factor kappa B (RANKL, also known as OPGL/ODF/TRANCE). RANKL, a member of the tumor necrosis factor (TNF) superfamily, regulates both osteoclast formation and function by binding to its receptor RANK expressed on osteoclast precursors and mature osteoclasts. The essential role of RANKL and RANK in the osteoclastogenic process has been demonstrated by the findings that mice lacking the gene for either protein develop osteopetrosis due to failure to form osteoclasts.

RANK (receptor activator of NF-κB) was identified as a member of the TNF receptor family. Members of the TNF receptor family lack intrinsic enzymatic activity. They usually transduce intracellular signals by recruiting various adaptor proteins such as TNF receptor associated factors (TRAFs) through specific motifs in the cytoplasmic domains. Since the unraveling of the RANKL/RANK system, efforts have been undertaken to elucidate RANK-initiated intracellular signaling. Many of these efforts have focused on the characterization of the receptor-proximal signaling events, which represent the initial components of RANK-mediated signaling. Although these studies have mapped RANK cytoplasmic regions by using in vitro binding assays, their physiological relevance to osteoclast biology remains largely unexplored.

The discovery of the RANKL/RANK/OPG regulatory axis has also raised high expectation for osteoprotegerin (OPG) and soluble RANK-Fc as therapeutic drugs for treating bone diseases. However, both OPG and RANK-Fc lack specificity, and the use of OPG or RANK-Fc may produce adverse effects on other biological processes that involve RANK, such as the development of immune system and mammary gland. Accordingly, there is a need for more specific RANK modulators and methods for identifying them.

SUMMARY OF THE INVENTION

The present invention is based on the identification of three PTM motifs which are responsible for osteoclast differentiation, function and survival. Each of these motifs plays a distinct role in the activation of RANK-mediated signaling pathways. The characterization of these motifs allows the identification of molecules that can modulate activities of specific PTM motifs and be used to treat osteoporosis, rheumatoid arthritis, or other RANK-related diseases.

In one aspect, the present invention provides methods for identifying agents capable of modulating RANK activity. These methods comprise:

contacting a ligand with one or more cells in the presence of a molecule of interest, where each cell comprises a chimeric protein which includes (1) a non-RANK sequence capable of binding to the ligand and (2) a sequence comprising one or more PTM motifs selected from the group consisting of PTM3, PTM5, and PTM6, and the treatment of the cell(s) with the ligand induces oligomerization of the chimeric protein and thereby activates a RANK-mediated signaling pathway in the cell(s); and detecting the activation level of the RANK-mediated signaling pathway in the cell(s) after the ligand treatment.

The activation level thus detected, as compared to a control level, is therefore indicative of whether the molecule of interest can modulate the RANK-mediated signaling pathway.

The chimeric protein employed in the invention preferably is a transmembrane protein which comprises a non-RANK extracellular domain and a RANK cytoplasmic domain including one or more functional PTM motifs. In certain examples, the non-RANK extracellular domain is an extracellular domain of a non-RANK TNFR superfamily member, such as TNFR1, TNFR2, Fas, or CD40.

The non-RANK extracellular domain can be selected such that the ligand employed can selectively bind to the domain, but not other proteins (e.g., endogenous membrane proteins) in the cell(s) that would trigger activation of RANK-mediated signaling pathways. This can be achieved, for example, by using a non-RANK extracellular domain heterologous to the cell(s). In a non-limiting example, the cell(s) can be murine cell(s), and the non-RANK extracellular domain is derived from a non-mouse protein, such as a human protein. In another example, the cell(s) can be human cell(s), and the non-RANK extracellular domain is derived from a non-human protein, such as a murine protein.

Cells suitable for the present invention include, but are not limited to, bone marrow macrophage cells, osteoclast precursor cells, or osteoclast cells. Other cells that include. RANK signaling machineries can also be used. Non-limiting examples of suitable cells include RAW264.7 or J774 cells.

In one embodiment, a chimeric protein, employed in the invention comprises a functional PTM3 motif but does not have any functional PTM5 or PTM6 motif. Cells comprising this chimeric protein can be used to identify molecules that are capable of inhibiting or otherwise modulating PTM3- mediated RANK signaling pathways (e.g., pathways that lead to the activation of NF-κB, JNK, ERK, p38, or Akt/PKB).

In another embodiment, a chimeric protein employed in the invention comprises a functional PTM5 motif but does not have any functional PTM3 or PTM6 motif. Cells comprising this chimeric protein can be used to identify molecules that are capable of inhibiting or otherwise modulating PTM5-mediated RANK signaling pathways (e.g., pathways that lead to the activation of NF-κB or p38).

In still another embodiment, a chimeric protein employed in the invention comprises a functional PTM6 motif but does not have any functional PTM3 or PTM5 motif. Cells comprising this chimeric protein can be used to identify molecules that are capable of inhibiting or otherwise modulating PTM6-mediated RANK signaling pathways (e.g., pathways that lead to the activation of NF-κB).

In a further embodiment, a chimeric protein employed in the invention comprises at least two functional PTM motifs, each of which is selected from the group consisting of PTM3, PTM5, and PTM6. Oligomerization of this chimeric protein activates at least two distinct RANK-mediated signaling pathways, each of which is selected from the a PTM3-mediated RANK signaling pathway, a PTM5-mediated RANK signaling pathway, or a PTM6-mediated RANK signaling pathway. Molecules capable of inhibiting or otherwise modulating these distinct signaling pathways can therefore be identified.

The activation level of a RANK-mediated signaling pathway in the cell(s) can be detected by a variety of means. For instance, the activation level can be determined by measuring the phosphorylation level of IκB, JNK, ERK, p38, or Akt/PKB. The activation level can also be evaluated by monitoring the expression level of a downstream gene that is regulated by NF-κB or AFX/FOXO4.

In addition, reporter assays can be used to detect the activation level of a RANK-mediated signaling pathway. In a non-limiting example, a reporter assay of the invention utilizes a reporter vector which comprises a reporter gene operably linked to a promoter that includes one or more NF-κB binding sites. The reporter vector is introduced into the cell(s) comprising a chimeric protein of the invention. Binding of the chimeric protein to a suitable ligand induces oligomerization of the protein which triggers a RANK-initiated signaling pathway. This in turn leads to the phosphorylation and degradation of IκB and therefore activation of NF-κB transcription factor. The activated NF-κB binds to the NF-κB binding site(s) in the promoter of the reporter gene, inducing (or suppressing) the expression of the reporter gene. As a result, the activation level of a RANK-mediated pathway can be determined by measuring the level of expression of the reporter gene in the cell(s). Reporter genes suitable for this purpose include, but are not limited to, green fluorescent protein, luciferase, horse radish peroxidase, alkaline phosphatase, galactosidase, or chloramphenicol acetyl transferase.

The present invention also features the use of reporter vectors that comprise a report gene operably linked to a promoter including one or more AFX/FOXO4 binding sites. These reporter vectors can be used to monitor the activation of RANK-mediated osteoclast survival signals. Molecules capable of modulating osteoclast survival can therefore be identified using the methods described herein.

In another aspect, the present invention features other methods for identifying agents capable of modulating RANK activity. These methods comprise:

contacting a ligand with one or more osteoclast precursor cells in the presence of a molecule of interest, where each cell comprises a chimeric protein which includes (1) a non-RANK sequence capable of binding to the ligand and (2) a sequence comprising one or more PTM motifs selected from the group consisting of PTM3, PTM5, and PTM6, and the treatment of the cell(s) with the ligand induces oligomerization of the chimeric protein and thereby activates a RANK-mediated signaling pathway in the cell(s); and detecting the level of osteoclastogenesis of the cell(s) after the ligand treatment.

The level of osteoclastogenesis thus detected, as compared to a control level, is indicative of whether the molecule of interest is capable of modulating RANK activity.

In still another aspect, the present invention features another method for identifying RANK modulators. This method comprises:

contacting a ligand with one or more osteoclast or osteoclast precursor cells in the presence of a molecule of interest, where each cell comprises a chimeric protein which includes (1) a non-RANK sequence capable of binding to, the ligand and (2) a sequence comprising one or more PTM motifs selected from the group consisting of PTM3, PTM5, and PTM6, and the treatment of the cell(s) with the ligand induces oligomerization of the chimeric protein and thereby activates a RANK-mediated signaling pathway in the cell(s); and detecting the survival level of the cell(s) after the ligand treatment.

The survival level thus detected, as compared to a control survival level, is indicative of whether the molecule of interest is capable of modulating RANK activity.

In yet another aspect, the present invention features another method for identifying RANK modulators. This method comprises:

contacting a ligand with one or more osteoclast precursor cells in the presence of a molecule of interest, where each cell comprises a chimeric protein which includes (1) a non-RANK sequence capable of binding to the ligand and (2) a sequence comprising one or more PTM motifs selected from the group consisting of PTM3, PTM5, and PTM6, and the treatment of the cell(s) with the ligand induces oligomerization of the chimeric protein and thereby activates a RANK-mediated signaling pathway in the cell(s); and detecting the bone resorption capability of the cell(s) after the ligand treatment.

The bone resorption capability thus detected, as compared to a control level, is indicative of whether the molecule of interest is capable of modulating RANK activity.

Any chimeric protein described herein can be used for the above-described methods.

The activation level of RANK-mediated signaling, the level of osteoclastogenesis or bone resorption, or the level of osteoclast survival can be compared to a control level to determine whether a molecule of interest modulates RANK activity. A control level can be a negative control level (e.g., a level measured using the same assay but absent the molecule of interest, or a level measured using the same assay in the presence of the molecule of interest except that the PTM(s) being investigate is deactivated in the chimeric protein). A control level can also be a positive control level (e.g., a level measured using the same assay in the presence of a known RANK modulator). In many cases, a control level is an average of levels measured under the control conditions.

The present invention further features RANK modulators that are identified according to the methods of the present invention and compositions comprising the same. In one example, a composition of the invention comprises a first agent capable of modulating PTM3-mediated RANK signaling and a second agent capable of modulating PTM5-mediated RANK signaling. In another example, a composition of the invention comprises a first agent capable of modulating PTM3-mediated RANK signaling and a second agent capable of modulating PTM6-mediated RANK signaling. In still another example, a composition of the invention comprises a first agent capable of modulating PTM5-mediated RANK signaling and a second agent capable of modulating PTM6-mediated RANK signaling. In a further example, a composition of the invention comprises an agent capable of modulating at least two RANK-mediated signal transduction pathways selected from the group consisting of a PTM3-mediated RANK signaling pathway, a PTM5-mediated RANK signaling pathway, and a PTM6-mediated RANK signaling pathway.

In addition, the present invention features the use of binding assays to screen for RANK modulators. These methods typically comprise:

detecting a level of binding between a first TRAF protein and a first polypeptide comprising a first PTM motif in the presence of a molecule of interest, where the first TRAF protein is capable of binding to the first PTM motif in the absence of the molecule of interest; and detecting a level of binding between a second TRAF protein and a second polypeptide comprising a second PTM motif in the presence of said molecule of interest, where the second TRAF protein is capable of binding to the second PTM motif in the absence of the molecule of interest.

The first and second PTM motifs can be selected from the group consisting of PTM3, PTM5, and PTM6. The binding level between the first TRAF and the first polypeptide, and the binding level between the second TRAF and the second polypeptide, as compare to control levels, are indicative of whether the molecule of interest is capable of modulating RANK activity.

Furthermore, the present invention features methods of modulating RANK activity in a cell of interest. These methods comprise contacting one or more agents with a cell to modulate at least two RANK-mediated signaling pathways in the cell, where each of the signaling pathways is selected from a PTM3-mediated RANK signaling pathway, a PTM5-mediated RANK signaling pathway, or a PTM6-mediated RANK signaling pathway. In one example, the cell is contacted with at least two agents, each of which inhibits a different respective RANK signaling pathway. The cell of interest can be, without limitation, an osteoclast cell or an osteoclast precursor cell.

The present invention further features methods for modulating RANK activity in a subject in need thereof. The methods comprise administering one or more agents to the subject to inhibit at least two RANK-mediated pathways in a cell of the subject (e.g., an osteoclast cell or an osteoclast precursor cell). Each of the RANK-mediated pathways can be selected from a PTM3-mediated RANK signaling pathway, a PTM5-mediated. RANK signaling pathway, or a PTM6-mediated RANK signaling pathway. Subjects suitable for this treatment include patients who have osteoporosis, rheumatoid arthritis-associated bone loss, cancer-induced osteolysis, or other RANK-related bone disorders.

The present invention also features chimeric proteins comprising an oligomerizable non-RANK extracellular domain and a RANK intracellular domain with one or more functional PTM motifs. Mutations can be introduced into the RANK intracellular domain to deactivate selected PTM motif(s).

Other features, objects, and advantages of the invention are apparent in the detailed description that follows. It should be understood, however, that the detailed description, while indicating preferred embodiments of the invention, is given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation.

FIGS. 2A-2C indicate that the chimeric receptor of FIG. 1B is capable of mediating osteoclast formation and function using TNFα as a surrogate.

FIGS. 3A-3C demonstrate that RANK contains multiple functional motifs capable of promoting osteoclast formation.

FIGS. 4A and 4B demonstrate that simultaneous mutation of all six PTMs in the RANK cytoplasmic domain blocks osteoclast differentiation.

FIG. 19 discloses SEQ ID NOS 1-3, respectively, in order of appearance.

DETAILED DESCRIPTION OF THE INVENTION

Figure 1:
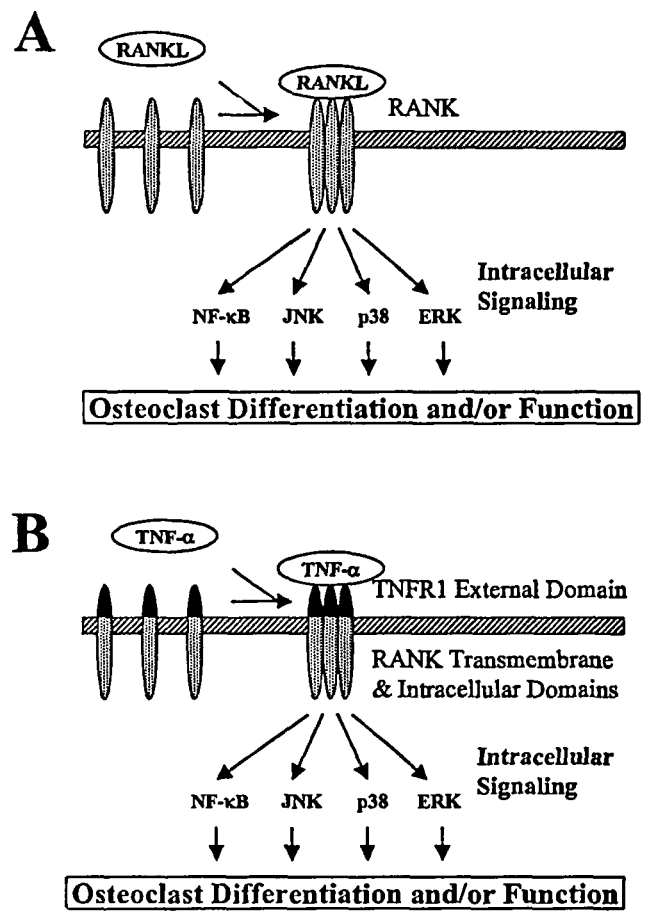
FIG. 1A schematically illustrates a model showing transmission of the endogenous RANK intracellular signaling in osteoclast formation and function.
FIG. 1B is a schematic diagram showing a chimeric receptor comprising the external domain of TNFR1 linked to the transmembrane and cytoplasmic domains of RANK. This figure also depicts how the chimeric receptor initiates RANK intracellular signaling required for osteoclast formation and function by using TNFα as a surrogate.

The present invention is based on the identification and characterization of three TRAF-binding motifs (PTMs) in the cytoplasmic domain of RANK—namely, PTM3, PTM5, and PTM6. Each of these motifs plays distinct roles in the activation of RANK-mediated intracellular signaling pathways and the mediation of osteoclast formation, function and survival. PTM3 can mediate NF-κB (nuclear factor kappa B), JNK (c-Jun N-terminal kinase), ERK (extracellular signal-regulated kinase) and p38 signaling pathways; PTM5 is capable of activating NF-κB and p38 signaling pathways; and PTM6 can activate NF-κB signaling pathway. PTM3 is also involved in osteoclast survival through mediating RANKL-induced activation of Akt/PKB, which leads to the phosphorylation of the downstream effector AFX/FOXO4.

PTM3 plays a predominant role in promoting osteoclast survival, but has a less prominent role in osteoclast formation and function. PTM5 and PTM6 are highly potent in osteoclast formation and function, but have only moderate effects on osteoclast survival. The revelation of the distinct functions of these RANK motifs allows for the identification of molecules that can selectively modulate RANK activities in osteoclastogenesis, mammary gland development, dendritic-cell/T-cell communication, or survival of leukemic or osteoclast cells. These RANK motifs also represent potential drug targets for osteoporosis, rheumatoid arthritis, cancer-induced bone lesions, T-cell or B-cell malignancies, and other RANK-related diseases.

In one aspect, the present invention provides methods for identifying or evaluating agents capable of modulating RANK-mediated signaling pathways. These methods typically include inducing oligomerization of a chimeric protein in a cell or a cell-free system, and detecting the activities of RANK-mediated signaling pathways in the cell or cell-free system. The chimeric protein employed can be a transmembrane protein comprising an oligomerizable extracellular domain and an intracellular domain including one or more PTMs selected from PTM3, PTM5, PTM6 or their functional equivalents. The oligomerization of the chimeric protein triggers activation of PTM-mediated RANK signaling pathways. The activation levels of these pathways in the presence of a molecule of interest can be detected and compared to control levels (e.g., activation levels measured in the absence of the molecule, or in the presence of the molecule but with a control protein in which the functional PTM(s) being investigated is deactivated). Molecules capable of inhibiting or otherwise modulating the activation levels of these pathways can therefore be identified.

Preferably, the extracellular domain of the chimeric protein can induce oligomerization (e.g., trimerization) of the chimeric protein upon binding to a non-RANKL ligand. Extracellular domains suitable for this purpose include, but are not limited to, the extracellular domains of non-RANK tumor necrosis, factor receptor superfamily members, such as TNFR1 (tumor necrosis factor receptor superfamily, member 1A), TNFR2 (tumor necrosis factor receptor superfamily, member 1B), Fas (tumor necrosis factor receptor superfamily, member 6), or CD40 (tumor necrosis factor receptor superfamily member 5). The extracellular domains of other receptor proteins whose activation can be triggered by oligomerization can also be used. In addition, other oligomerizable polypeptides or protein fragments can be used. Non-limiting examples of these polypeptides/protein fragments include antigenic polypeptides that can form trimers or oligomers when bound to their corresponding antibodies.

The extracellular domain of a chimeric protein employed in the invention can be selected such that its ligand can selectively induce oligomerization of the chimeric protein, but not other receptor proteins in the cell that would trigger activation of RANK-associated signaling pathways. This can be achieved, for example, by using an extracellular domain that is heterologous to the cell. In a non-limiting example, the cell employed is a murine (or human) cell, while the extracellular domain of the chimeric protein is derived from a non-mouse (or non-human) protein such that the ligand for the extracellular domain does not bind to any murine (or human) receptor proteins. Extracellular domains whose ligands can activate other receptor proteins may also, be used, provided that the signaling activities mediated by the chimeric protein can be distinguished from those mediated by other receptor proteins.

PTMs suitable for the present invention include, but are not limited to, murine or human PTMs or their functional equivalents. PTMs of other species may also be used. These PTMs are capable of recruiting respective TRAFs upon oligomerization or activation of the chimeric protein. At least six TRAF family members have been identified (TRAFs 1-6). Each TRAF protein contains a ring and zinc finger motif in its N- or C-terminal domain which can mediate self association and protein interaction. See, e.g., Inoue, et al., Exp. Cell Res., 254:14-24. (2000).

TRAF1 and TRAF2 can form a heterodimeric complex, which involves in TNFα-mediated activation of MAPK8/JNK and NF-κB. The protein complex formed by TRAF1 and TRAF2 also interacts with inhibitor-of-apoptosis proteins (IAPs), and thus mediates the anti-apoptotic signals from TNF receptors. The expression of this protein can be induced by Epstein-Barr virus (EBV). EBV infection membrane protein 1 (LMP1) is found to interact with this and other TRAF proteins; this interaction is thought to link LMP1-mediated B lymphocyte transformation to the signal transduction from TNFR family receptors. Multiple alternatively-spliced transcript variants have been found for TRAF2 gene, but the biological validity of only one transcript has been determined.

TRAF3 has been reported to function in the signal transduction of CD40, a TNFR family member important for the activation of the immune response. TRAF3 is found, to be a critical component of the lymphotoxin-β receptor (LTbetaR) signaling complex, which induces NF-κB activation and cell death initiated by LTbeta ligation. Epstein-Barr virus-encoded latent infection membrane protein-1 (LMP1) can interact with this and several other members of the TRAF family, which may be essential for the oncogenic effects of LMP1. Three alternatively-spliced transcript variants encoding two distinct isoforms have been reported.

TRAF4 has been shown to interact with neurotrophin receptor, p75 (NTR/NTSR1), and negatively regulate NTR induced cell death and NF-κB activation. This protein has been found to bind to p47phox, a cytosolic regulatory factor included in a multi-protein complex known as NAD(P)H oxidase. This protein is thought to be involved in the oxidative activation of MAPK8/JNK. Two alternatively-spliced transcript variants of this gene encoding distinct isoforms have been reported.

TRAF5 has been found to be one of the components of a multiple protein complex associated with the CD40 cytoplasmic domain, which mediates TNF induced NF-κB activation and protection from cell death. This protein has also been implicated in the signaling events mediated by various other receptors including CD27, CD30, and lymphotoxin-beta receptor. Two alternatively-spliced transcript variants encoding the same protein have been reported.

TRAF6 mediates the signaling not only from the members of the TNF receptor superfamily, but also from the members of the Toll/IL-1 family. Signals from receptors such as CD40, RANK and IL-1 have been shown to be mediated by this protein. TRAF6 also interacts with various protein kinases including IRAK1/IRAK, SRC and PKCzeta, which provides a link between distinct signaling pathways. TRAF6 functions as a signal transducer in the NF-κB pathway that activates TO kinase (IKK) in response to proinflammatory cytokines. The interaction of TRAF6 with UBE2N/UBC13, and UBE2V1/UEV1A, which are ubiquitin-conjugating enzymes catalyzing the formation of polyubiquitin chains, has been found to be required for IKK activation by this protein. Two alternatively-spliced transcript variants encoding identical proteins have been reported.

TRAFs 1, 2, 3, 5 and 6 have been reported to interact with various parts of the RANK cytoplasmic domain both in vitro and in cells. See, for example, Darnay, et al., J. Biol. Chem., 273:20551-20555 (1998); Galibert, et al., J. Biol. Chem., 273: 34120-34127 (1998); Wong, et al., J. Biol. Chem., 273:28355-28359 (1998); Darnay, et al., J. Biol. Chem., 274:7724-7731 (1999); Kim, et al., FEBS Letters, 443:297-302 (1999); and Ye, et al., Nature, 418:443-44 (2002). All of these references are incorporated herein by reference in their entireties.

In one embodiment, the chimeric proteins employed in the present invention comprise an endogenous RANK cytoplasmic domain which includes PTM3, PTM5, or PTM6. Non-limiting examples of suitable RANK cytoplasmic domains include the intracellular domains of murine and human RANK proteins. Murine and human RANK proteins have Entrez accession numbers NP_033425 (SEQ ID NO: 32) and NP_003830 (SEQ ID NO: 33), respectively. Their amino acid sequences are depicted in SEQ ID NO: 32 and SEQ ID NO:33, respectively. The intracellular domain of murine RANK protein consists of amino acid 235 to 625 of SEQ ID NO:32, and the intracellular domain of human RANK protein consists of amino acids 232 to 616 of SEQ ID NO:33. Cytoplasmic domains of other RANK proteins can also be used. RANK genes of other species can be readily identified based on murine or human sequences. Methods suitable for this purpose include, but are not limited to, genomic or cDNA library screens or genome BLAST searches. Genomes of many species are available at Entrez (National Center for Biotechnology Information, Bethesda, Md. 20894). The RANK gene of a species of interest can be identified through BLAST searching the genome of interest by using the murine or human sequence as the query sequence. The cytoplasmic domain of a RANK gene thus identified can be determined by using transmembrane prediction programs, such as TMHMM, or other suitable means known in the art.

In another embodiment, the chimeric proteins employed in the present invention include one or more fragments of an endogenous RANK cytoplasmic domain. Each fragment includes one or more PTM motifs selected from PTM3, PTM5, or PTM6, and can bind to a respective TRAF protein upon oligomerization of the chimeric protein to activate the downstream signaling pathway. Suitable PTMs for this purpose include murine and human PTMs. PTMs of other species can also be employed. Murine PTM3, PTM5, and PTM6 motifs comprise PFQEP (SEQ ID NO:1; amino acids 369-373 of NP_033425 (SEQ ID NO: 32)), PVQEET (SEQ ID NO:2; amino acids 560-565 of NP_033425 (SEQ ID NO: 32)), and PVQEQG (SEQ ID NO:3; amino acids 604-609 of NP_033425 (SEQ ID NO: 32)), respectively; and human PTMS, PTM5, and PTM6 motifs comprise PFSEP (SEQ ID NO:4; amino acids 373-377 of NP_003830 (SEQ ID NO: 33)), PVQEET (SEQ ID NO:2; amino acids 569-574 of NP_003830 (SEQ ID NO: 33)), and PVQEQG (SEQ ID NO:3; amino acids 607-612 of NP_003830 (SEQ ID NO: 33)), respectively.

Amino acid residues surrounding SEQ ID NOs:1-4 in the endogenous RANK cytoplasmic domains can also be included in a chimeric protein to improve its interaction with TRAF protein(s). For instance, a chimeric protein of the present invention can include a mouse RANK cytoplasmic domain consisting of GSKSIPPFQEPLEV-GENDSLSQCFTGTESTV (SEQ ID NO:5), EPESEPVGR-PVQEETL AHRDSFAG (SEQ ID NO:6), or TSRPVQEQG-GAQT (SEQ ID NO:7). A chimeric protein of the present invention can also include a human RANK cytoplasmic domain consisting of GSKSTPPFSEPLEV-GENDSLSQCFTGTQSTV (SEQ ID NO:8), AEPMGR-PVQEETLARRDSFAG (SEQ ID. NO:9) or ASRPVQEQG-GAK (SEQ ID NO:10).

Fragments of SEQ ID NOs:5-10 can also be used. Each fragment includes at least a PTM sequence selected from SEQ ID NOs:1-4, and is capable of binding to a respective TRAF protein upon oligomerization of the chimeric protein. In many cases, each of these fragments includes an endogenous. RANK cytoplasmic sequence consisting of from about 5 to about 10, from about 10 to about 20, or from about 20 to about 30 amino acid residues selected from SEQ ID NOs:5-10.

Each chimeric protein of the present invention can include 1, 2, 3 or more PTMs selected from PTM3, PTM5, and PTM6. A chimeric protein of the invention can also include deactivated PTM motif(s). For instance, a chimeric protein can include a functional PTM3 but does not have any functional PTM5 or PTM6. A chimeric protein can also include a functional. PTM5 but does not have any functional PTM3 or PTM6. Likewise, a chimeric protein can include a functional PTM6 but does not have any functional PTM3 or PTM5. Each functional PTM is capable of activating its corresponding signaling pathway upon oligomerization of the chimeric protein, e.g., a PTM3-mediated RANK signaling pathway, a PTM5-mediated RANK signaling pathway, or a PTM6-mediated RANK signaling pathway. PTMs in a chimeric protein of the invention can be derived from the same or different species.

In still another embodiment, a chimeric protein of the invention comprises an extracellular domain of a non-RANK TNF receptor superfamily member (e.g., TNFR1, TNFR2, Fas, or CD40), and a RANK cytoplasmic domain with mutations in one or more PTMs. Suitable PTM mutations include, but are not limited to, those described in FIG. 3A. Other mutations can also be used. These mutations typically include substitutions, deletions, or additions of amino acid residues in or around the PTM(s) that is to be deactivated. These mutations disrupt or significantly reduce the interactions of the selected PTM(s) with its downstream effector(s). Preferably, these mutations do not prevent the chimeric protein from oligomerization upon binding to its ligand.

In a non-limiting example, a chimeric protein of the invention comprises a RANK cytoplasmic domain in which the PTM5 and PTM6 motifs are deactivated while the PTM3 motif remains functional. Oligomerization of this chimeric protein activates the PTM3-mediated pathways, such as the NF-κB pathway, the Akt/PKB pathway, the JNK pathway, the ERK pathway, or the p38 pathway. In another example, a chimeric protein of the invention comprises a RANK cytoplasmic domain in which the PTM3 and PTM6 motifs are deactivated while the PTM5 motif remains functional. Oligomerization of the chimeric protein activates the PTM5-mediated pathways, such as the NF-κB pathway or the p38 pathway. In still another example, a chimeric protein of the invention comprises a RANK cytoplasmic domain in which the PTM3 and PTM5 motifs are deactivated while the PTM6 motif remains functional. Oligomerization of this protein activates the PTM6-mediated pathways, such as the NF-κB pathway.

The extracellular and cytoplasmic domains of a chimeric protein can be derived from the same species. For instance, both the extracellular and cytoplasmic domains can be derived from murine (or human) sequences. The extracellular and cytoplasmic domains of a chimeric protein can also be derived from different species. For instance, the extracellular domain can be derived from a human sequence (e.g., human TNFR1, TNFR2, Fas, or CD40), while the cytoplasmic domain is derived from a murine sequence (e.g., murine RANK protein), and vice versa. The extracellular domain of a chimeric protein can include either a full-length extracellular sequence of a non-RANK TNF receptor superfamily member, or a fragment thereof, provided that the fragment can bind to a ligand to induce oligomerization of the chimeric protein. Exemplary ligands for TNFR1/TNFR2, Fas, and CD40 include, but are not limited to, TNF, FASL, and CD40L, respectively. Preferably, soluble ligands (e.g., soluble FASL or CD40L extracellular domains) are used to induce oligomerization of the corresponding chimeric proteins. FASL or CD40L expressed on cell surfaces can also be used. Contacting such a cell with a cell that expresses a chimeric protein comprising a Fas or CD40 extracellular domain will induce oligomerization of the chimeric protein, thereby activating RANK-mediated signaling pathways in the cell. Antibodies specific for the extracellular domains of TNFR1, TNFR2, Fas, or CD40 can also be used to trigger oligomerization of chimeric proteins that comprise these extracellular domains. Other oligomerizable polypeptides, such as those capable of being clustered via antibodies, can also be used.

The present invention further contemplates the use of non-transmembrane proteins for the identification of RANK modulators. These non-transmembrane proteins include one or more PTMs capable of interacting with corresponding TRAFs to activate the downstream signaling pathways. Each of the PTMs is selected from PTM3, PTM5 or PTM6. In many cases, the non-transmembrane proteins are cytosolic proteins which include a domain that can trigger protein oligomerization upon occurrence of a specified event, such as binding to a ligand or changing in the ionic strength. In certain cases, the non-transmembrane proteins can activate RANK signaling without a triggering event.

A variety of methods can be used to assess the activation of PTM-mediated RANK signaling pathways. Exemplary methods include, but are not limited to, those suitable for detecting or monitoring the activities of NF-κB, JNK, ERK, p38, or Akt/PKB signaling pathways. Specific methods are described in the Examples, infra, which involve the detection of phosphorylation of IκB, JNK, ERK, p38 or Akt/PKB. RANK modulators can be identified by comparing the phosphorylation level of NB, JNK, ERK, p38 or Akt/PKB in the presence of a molecule of interest to a control phosphorylation level measured in the absence of the molecule. Methods suitable for this purpose include, but are not limited to, gel scanners, gel imagers, or gel densitometers. In many cases, modulators thus identified can inhibit phosphorylation of IκB, JNK, ERK, p38, or Akt/PKB by at least 2, 3, 4, 5, or more folds.

The activation of PTM-mediated RANK signaling pathways can also be evaluated by monitoring osteoclast formation, function or survival. Methods suitable for this purpose include, but are not limited to, osteoclastogenesis, bone resorption or osteoclast survival assays. See, for example, Examples 1 and 6 (infra); Armstrong, et al., J. Biol. Chem., 277:44347-44356 (2002); and Ye, et al. (supra). A typical osteoclastogenesis assay includes introducing a chimeric protein of the present invention into an osteoclast precursor cell, such as a bone marrow macrophage or a splenic hematopoietic progenitor cell, followed by adding a ligand to induce oligomerization of the chimeric protein, thereby initiating cellular differentiation. Molecules capable of inhibiting or interfering with osteoclast differentiation can be identified by comparing the level of osteoclastogenesis in the presence of the molecules to that in the absence of the molecules. In many cases, molecules thus identified can reduce osteoclast differentiation or osteoclastogenesis by at least 30%, 40%, 50%, 60%, 70%, 80%, 90% or 100%.

Methods suitable for introducing a chimeric protein, or an expression vector encoding the same, into a cell of interest are well known in the art. Expression vectors suitable for this purpose include, for example, viral vectors such as retroviral, lentiviral, adenoviral, adeno-associated viral (AAV), herpes viral, alphavirus, astrovirus, coronavirus, orthomyxovirus, papovavirus, paramyxovirus, parvovirus, picornavirus, poxvirus, or togavirus vectors. Liposomally-encapsulated expression vectors can also be used.

In addition, osteoclast bone resorption and osteoclast survival assays can be used to evaluate activities of PTM-mediated RANK signaling pathways. RANK modulators capable of inhibiting osteoclast bone resorption (or osteoclast survival) can be identified by comparing the level of bone resorption (or osteoclast survival) in the presence of the modulators to a control level (e.g., a level measured in the absence of the modulators, or in the presence of the modulators but using a control protein in which the PTM(s) being investigated is deactivated). In many cases, modulators thus identified can inhibit osteoclast-dependent bone resorption (or osteoclast survival) activities by at least 30%, 40%, 50%, 60%, 70%, 80%, 90% or 100%.

The present invention also features the use of reporter assays to screen for RANK modulators. Suitable reporter assays include, but are not limited to, those described in Galibert, et al. (1998, supra), Darnay, et al. (1999, supra), and Ye, et al. (supra). In one embodiment, a reporter assay of the invention employs a reporter vector which comprises a reporter gene operably linked to a promoter including one or more NF-κB binding sites. The reporter vector is introduced into a cell which expresses a chimeric protein of the invention. Oligomerization of the chimeric protein upon ligand binding triggers phosphorylation and degradation of IκB, which, in turn activates NF-κB. The activated NF-κB translocates into the nucleus, binding to the NF-κB binding site(s) in the promoter of the reporter gene and thereby activating the expression of the reporter gene. A molecule of interest can be added to the cell. A reduction in the expression level of the reporter gene in the presence of the molecule of interest, as compared to a control expression level (e.g., a level measured in the absence of the molecule, or in the presence of the molecule but using a control chimeric protein in which the PTM(s) being investigated is deactivated), is indicative that the molecule of interest is capable of inhibiting the RANK signaling mediated by the chimeric protein. In many cases, molecules thus identified can inhibit the expression of the reporter gene by at least 2, 3, 4, 5, or more folds.

NF-κB is a ubiquitous transcriptional factor. It was originally identified as a protein complex consisting of a 65 kDa DNA binding subunit and an associated 50 kDa protein. The 65 kDa subunit, also referred to as Rel A, is functionally related to c-Rel p75. The p50 subunit of NF-κB is derived from the amino terminus of a precursor designated p105. A second protein designated p52 (previously referred to as p49) has also been identified and can act as an alternative to p50 in NF-κB heterodimers.

Many genes involved in cell proliferation and apoptosis contain NF-κB binding sites in their promoter regions. Activated NF-κB can bind to these sites to activate the expression of the downstream genes. A consensus NF-κB binding sequence is depicted in SEQ ID NO:34. Specific examples of NF-κB binding sites are illustrated in SEQ ID NOs:35 and 36. Other NF-κB binding sequences, such as that described in Lavrovsky, et al., PROC. NATL. ACAD. SCI., 91:5987-5991 (1994), can also be used.

In addition, the present invention contemplates the use of promoters containing inhibitory NF-κB binding sites. Binding of NF-κB to these sites inhibits the expression of the downstream reporter genes. Non-limiting examples of such promoters include murine $\alpha_1(I)$ and human $\alpha_2(I)$ collagen promoters. An exemplary inhibitory NF-κB binding site is described in Novitskiy, et al., J. BIOL. CHEM., 279:15639-15644 (2004), the sequence of which is depicted in SEQ ID NO:37. Where an inhibitory NF-κB site is used, the expression level of the reporter gene can be monitored for any increase caused by the presence of a molecule of interest, as compared to a control expression level (e.g., in the absence of the molecule, or in the presence of the molecule but using a control chimeric protein in which the PTM(s) being investigated is deactivated). Molecules capable of enhancing the expression of the reporter gene can be identified. In many cases, molecules thus identified can increase the expression level of the reporter gene by at least 2, 3, 4, 5, or more folds. These molecules are RANK modulators that can inhibit RANK signaling. The NF-κB binding site(s) employed in the invention can be located 100 to 2,000 bp upstream from the start of transcription (e.g., the TATA box) of the reporter gene. NF-κB binding sites located within 100 bp or beyond 2,000 bp may also be used. In addition, more than one NF-κB binding sites can be included in the promoter of the reporter gene to improve the sensitivity or selectivity of detection. For instance, at least 2, 3, 4, 5, or more NF-κB binding sites can be included in the promoter of the reporter gene. These sites can have the same or different NF-κB binding sequences.

In another embodiment, a reporter assay of the present invention employs a reporter vector which comprises a reporter gene operably linked to a promoter including one or more AFX/FOXO4 binding sites. A consensus AFX/FOXO4 binding sequence is depicted in SEQ ID NO:38. Specific examples of AFX/FOXO4 binding sites are described in SEQ ID NOs:39 and 40. See, also Tang, et al., J. BIOL. CHEM., 277:14255-14265 (2002). The expression vector is introduced into a cell comprising a chimeric protein of the invention. Oligomerization of the chimeric protein upon ligand binding activates Akt/PKB, which leads to the phosphorylation and inactivation of AFX/FOXO4, thereby reducing the expression of the reporter gene. The expression level of the reporter gene can be evaluated in the presence or absence of a molecule, of interest. Molecules capable of inhibiting the suppression of the reporter gene can therefore be identified. These molecules are modulators for osteoclast survival and are capable of blocking the RANK-mediated activation of Akt/PKB.

Reporter genes suitable for the present invention include those genes whose expression products are detectable by spectroscopic, photochemical, biochemical, enzymatic, immunochemical, electrical, optical, chemical, or other means. Exemplary reporter genes include, but are not limited to, fluorescent proteins (e.g. green fluorescent protein (GFP), red fluorescent protein (RFP), or blue fluorescent protein (BFP)), enzymes. (e.g., luciferase, horse radish peroxidase, alkaline phosphatase, β-galactosidase, or chloramphenicol acetyl transferase (CAT)), or surface antigens for which specific antibodies are available. Reporter gene activity in cells or cell lysates can be analyzed by standard methods, such as luminometry for luciferase activity or fluorescence microscopy for fluorescent proteins.

Cells that are amenable to the reporter assays of the present invention include, but are not limited to, bone marrow macrophages, osteoclast cells, or osteoclast precursor cells. These cells can be human or non-human cell lines or primary cell cultures. Specific examples of these cells include murine macrophage RAW cell lines (e.g., RAW 264.7 with ATCC #TIB71), and murine macrophage J774 cell lines (e.g., .J774.1 with ATCC #TIB67). Other cells that include RANK signaling machineries (such as those required for the activation of NF-κB or Akt/PKB) can also be used.

The reporter assays of the present invention typically involve contacting a test agent with a cell comprising a chimeric protein of the invention and a reporter vector; and detecting expression of the reporter gene. The expression level of the reporter gene, as compared to a control, indicates that the test agent modulates the activity of the RANK-mediated signaling pathway (e.g., the NF-κB or AFX/FOXO4 pathway). The test agent can be virtually any type of molecule. It can exist as a single isolated molecule, or can be a member of a chemical library (e.g. a combinatorial library).

Where the change in the expression level of the reporter gene is determined with respect to a control, the control can be a negative control, e.g. the same assay absent the test agent or with the test agent at a lower concentration. Another suitable negative control uses the same assay but with a different chimeric protein in which the PTM(s) being investigated is deactivated. Alternatively, or in addition, the control can be a positive control, e.g. the same assay run with an agent known to inhibit or otherwise modulate RANK-mediated signaling pathways.

A change in the expression level of the reporter gene is preferably a statistically significant change, e.g. as determined using any statistical test suited for the data set provided (e.g. t-test, analysis of variance, semiparametric techniques, or non-parametric techniques, such as Wilcoxon Mann-Whitney Test, Wilcoxon Signed Ranks Test, Sign Test, or Kruskal-Wallis Test). Preferably, the statistically significant change is significant at least at the 85%, more preferably at least at the 90%, still more preferably at least at the 95%, and most preferably at least at the 98% or 99% confidence level. In many examples, the change is at least a 10%, 20%, 50%, 100%, 200%, 300%, 400%, or 500% change as compared to a negative control.

The reporter assays of the invention can take place in a wide variety of formats. For instance, a single test agent can be screened with one or more cell lines. In addition, multiple agents can be screened against one or more cell lines at the same time. This can be accomplished by contacting different test agents with each cell line in a separate reaction vessel or well. Alternatively, multiple test agents can be assayed in a single assay. Those assays that test positive are then deconvolved in subsequent assays to determine which of the test agents in the positive screen was responsible for the positive signal.

The reporter assays of the invention can be run in any convenient format. In one embodiment, the assays are run in a multi-well format (e.g. a 96- or 384-well plate) suitable for high throughput screening. Other high throughput screening methods can also be used.

In one example, a combinatorial chemical library is employed to screen for RANK modulators. A combinatorial chemical library is a collection of diverse chemical compounds generated by either chemical synthesis or biological synthesis by combining a number of chemical building blocks. For example, a linear combinatorial chemical library (such as a polypeptide library) is formed by combining a set of chemical building blocks (e.g., amino acids) in many possible ways for a given compounds length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptides, peptoids, random bio-oligomers, benzodiazepines, diversomers (e.g., hydantoins), benzodiazepines and dipeptides, vinylogous polypeptides, nonpeptidal peptidomimetics with a β-D-glucose scaffolding, oligocarbamates, peptidyl phosphonates, peptide nucleic acids, antibodies, carbohydrates, or small organic molecule libraries (e.g., benzodiazepines, isoprenoids, thiazolidinones and metathiazanones, pyrrolidines, morpholino compounds, or benzodiazepines libraries).

Any chimeric protein described herein can be used in a reporter assay of the invention. In one embodiment, the reporter assay employs a chimeric protein which includes an extracellular domain that is heterologous to the host cell and a RANK cytoplasmic domain comprising a functional PTM selected from PTM3, PTM5, or PTM6. Preferably, the RANK cytoplasmic domain contains only one functional PTM selected from PTM3, PTM5, and PTM6, and the remaining two PTMs are deactivated by mutations. This allows for the identification of molecules that modulate the activities of the selected PTM motif.

The extracellular domain can be selected such that its ligand selectively induces oligomerization (e.g., trimerization) of the chimeric protein, but not other endogenous proteins in the host cell (e.g., endogenous RANK or TNFR proteins). Preferably, the ligand for the extracellular domain does not activate NF-κB in the host cell via receptors other than the chimeric protein. Non-limiting examples of suitable extracellular domains include the extracellular domains of heterologous TNF receptor superfamily members, such as heterologous TNFR1, TNFR2, Fas, or CD40. In one example, the host cell employed is a murine RAW or J774 cell, and the extracellular domain of the chimeric protein is derived from a human TNFR1, TNFR2, Fas, or CD40 protein.

The host cell employed further comprises a reporter vector, which includes a reporter gene operably linked to a promoter comprising one or more NF-κB binding sites (e.g., 1, 2, 3, 4, 5, or more NF-κB binding sites). Binding of NF-κB to the NF-κB site(s) activates (or inhibits) the expression of the reporter gene. Changes in the expression of the reporter gene can be detected using conventional means.

To identify molecules capable of inhibiting or otherwise modulating RANK signaling, a test agent can be added to the host cell. A suitable ligand is added to trigger oligomerization of the chimeric protein. The expression level of the reporter gene is then detected in the presence of the test agent, and compared to a control level (e.g., a level measured in the absence of the test agent, or in the presence of the test agent but using a different chimeric protein in which the PTM(s) being investigated is deactivated by mutations). A statistically significant difference between the expression level of the reporter gene in the presence of the test agent and the control level is indicative that the test agent is a RANK modulator. In many examples, a test agent thus identified can inhibit the expression of the reporter gene by at least 10%, 20%, 30%, 40%, 50%, 60%, 70%, 80%, 90%, or 100%, as compared to a control level. In many other examples, a test agent thus identified can increase the expression of the reporter gene by at least 10%, 20%, 30%, 40%, 50%, 60%, 70%, 80%, 90%, 100%, 200%, 300%, 400%, or more.

In another example, the chimeric protein employed in a reporter assay comprises a RANK cytoplasmic domain in which the PTM3 and PTM5 motifs are deactivated. This protein retains a functional PTM6 motif capable of mediating RANK signaling. Molecules capable of modulating (e.g., inhibiting) PTM6-mediated signaling can therefore be identified according to the methods described above. In a further example, the chimeric protein employed in a reporter assay comprises a RANK cytoplasmic domain with deactivated PTM3 and PTM6 motifs. This protein retains a functional PTM5 motif capable of mediating RANK signaling. Accordingly, molecules capable of modulating (e.g., inhibiting) PTM5-mediated signaling can be identified using the methods described herein. Likewise, a chimeric protein in which PTM5 and PTM6 motifs are deactivated can be used in a reporter assay to screen for molecules that are capable of modulating (e.g., inhibiting) PTM3-mediated RANK signaling.

The present invention also features the use of commercial kits for the detection of RANK-mediated NF-κB activation. Non-limiting examples of these commercial kits include the NFkappaB p65/p50 Transcription Factor Assays provided by CHEMICON International, Inc. (Temecula, Calif.). The assays employ a double-stranded biotinylated oligonucleotide containing a consensus sequence of the NF-κB binding sites. Host cells comprising a chimeric protein of the invention can be treated with a suitable ligand to induce oligomerization of the protein. The biotinylated oligonucleotide is then mixed with the cellular or nuclear extract of the cells, to allow binding of any activated NF-κB to the consensus sequence. After incubation, the mixture is transferred to a streptavidin-coated plate. The biotinylated double-stranded oligonucleotide bound by active NF-κB protein is immobilized and any inactive, unbound material is washed away. The bound NF-κB protein is subsequently detected using antibodies. A test agent can be added to the above assay, and the level of the bound NF-κB in the presence of the test agent is compared to a control level (e.g., a level measured using the same assay but absent the test agent, or in the presence of the test agent but with a different chimeric protein in which the PTM(s) being investigated is deactivated). A change (e.g., reduction) in the level of the bound NF-κB is indicative that the test agent is capable of modulating (e.g., inhibiting) the RANK-mediated NF-κB activation.

In another aspect, the present invention features methods of using binding assays to identify RANK modulators. These methods include detection and comparison of the binding levels between a PTM-containing protein and a corresponding TRAF in the presence or absence of a molecule of interest. The PTM motif in the PTM-containing protein can bind to the TRAF protein in the absence of the molecule of the interest. A change in the PTM-TRAF binding due to the presence of the molecule of interest is indicative of the molecule's ability to modulate (e.g., enhance or inhibit) the PTM-TRAF interaction and, therefore, the PTM-mediated RANK signaling pathway(s). Any PTM-containing protein may be employed in the binding assays of the present invention. In many embodiments, the PTM-containing proteins include or consist of an endogenous RANK cytoplasmic domain, such as SEQ ID NOs: 1-10.

In one embodiment, a RANK modulator identified by the present invention is capable of modulating the binding activities between two different PTM motifs and their respective TRAF proteins, whereas the two different PTMs are selected from PTM3, PTM5, and PTM6. Such a RANK modulator can be identified by (1) detecting the binding level between a first PTM (or a protein comprising the same) and a corresponding TRAF in the presence or absence of a molecule of interest, and (2) detecting the binding level between a second PTM (or a protein comprising the same) and a corresponding TRAF in the presence or absence of the same molecule. A change in both binding levels in the presence of the molecule, as compared to corresponding binding levels in the absence of the molecule, is indicative of the ability of the molecule to modulate two different PTM-TRAF interactions and, therefore, two different RANK signaling pathways. In one example, a RANK modulator thus identified can inhibit both PTM5-TRAF and PTM6-TRAF interactions. In another example, a RANK modulator thus identified can inhibit both PTM3-TRAF and PTM6-TRAF interactions. In still another example, a RANK modulator thus identified can inhibit both PTM3-TRAF and PTM5-TRAF interactions. In many cases, a RANK modulator can inhibit or enhance a desired PTM-TRAF interaction by at least 30%, 40%, 50%, 60%, 70%, 80%, 90% or 100%.

Exemplary methods suitable for assessing PTM-TRAF interactions include, but are not limited to, surface plasmon resonance (e.g., Biacore), radioimmune based assays, and fluorescence polarization binding assays. In one example, competitive assays are used for the identification of PTM-TRAF inhibitors. In such an assay, TRAF and a candidate molecule are combined with a PTM-containing protein under appropriate conditions. Either PTM or TRAF can be labeled with a detectable moiety so that the binding can be measured and the effectiveness of an inhibitor or enhancer determined. The detectable moiety allows for detection by direct or indirect means. Direct means include, but are not limited to luminescence, chemiluminescence, fluorescence, radioactivity, optical or electron density. Indirect means include, but are not limited to, enzymes or epitope tags.

A detectable moiety can be a compound or molecule that is distinguishable from the surroundings. The art is replete with examples of detectable moieties that can be used in screening assays. In the present specification, the term "label" is used interchangeably with "detectable moiety." A detectable moiety can be a moiety based on luminescence, chemiluminescence, fluorescence, radioactivity, enzymatic reactions, colorimetric, optical or electron density. It is to be understood that the screening assays described herein for identifying test compounds that influence the TRAF/PTM interaction may employ one or more of the detectable moieties known in the art. The TRAF or PTM-containing protein can be directly or indirectly labeled with a detectable moiety. Such moieties can be attached or labeled to the TRAF or PTM-containing protein by any suitable conventional procedure. For instance, the TRAF or PTM-containing protein comprises functional groups on amino acid side chains that can be reacted with functional groups on a desired moiety to form covalent bonds. Alternatively, the TRAF or PTM-containing protein can be derivatized to generate or attach a desired reactive functional group. The derivatization can involve attachment of one or more linkers or couplers, such as the bifunctional coupling reagents available for attaching molecules to polypeptides.

Molecules that inhibit or prevent the dissociation of the TRAF/PTM complex can be identified by forming, the complex in the absence of a candidate molecule, then adding the candidate molecule to the mixture, and changing the conditions so that, but for the presence of the candidate molecule, TRAF would be released from the complex. The concentration of the free or bound TRAF can then be measured and the dissociation constant of the complex could be determined and compared to a control.

Another method by which molecules can be identified that affect (either inhibit or promote) the interaction between TRAF and PTM-containing protein is the solid phase method, in which PTM-containing protein is bound and placed in a medium with labeled TRAF. The amount of signal produced by the interaction between TRAF and PTM-containing protein is measured in the presence and in the absence of a candidate molecule. Diminished levels of signal, in comparison to a control, indicate that the candidate molecule inhibits the interaction between TRAF and PTM-containing protein. Increased levels of signal, in comparison to a control, indicate that the candidate molecule promotes the interaction between TRAF and PTM-containing protein. In alternative embodiments, TRAF can be bound and PTM-containing protein labeled. The TRAF or PTM-containing protein can be directly or indirectly labeled. For example, if the protein is recombinantly produced, one can engineer fusion proteins including a polypeptide tag that can facilitate solubility, labeling, immobilization or detection of the fusion proteins. Polypeptide tags suitable for this purpose include, but are not limited to, streptavidin tags, FLAG tags, poly-histidine tags, glutathione S-transferase, or Fc fragments.

In many embodiments, homogeneous assay formats are used; such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence. In another aspect, the inventive methods utilize heterogeneous assay formats such as enzyme-linked immunosorbant assays (ELISA) or radioimmunoassays.

One such assay is based on fluorescence resonance energy transfer (FRET) between two fluorescent labels, an energy donating long-lived chelate label and a short-lived organic acceptor. The energy transfer occurs when the two labels are brought in close proximity via the molecular interaction between PTM and TRAF. In a FRET assay for detecting inhibition of the binding of PTM and TRAF, europium chelate or cryptate labeled PTM or TRAF serves as an energy donor and streptavidin-labeled allophycocyanin (APC) bound to the appropriate binding partner (i.e., PTM-containing protein if TRAF is labeled, or TRAF if PTM-containing protein is labeled) serves as an energy acceptor. Once PTM associates with TRAF, the donor and acceptor molecules are brought in close proximity, and energy transfer occurs, generating a fluorescent signal at 665 nm. Inhibitors of the interaction of PTM and TRAF will thus reduce the fluorescent signal, whereas enhancers of this interaction would increase it.

Another useful assay is a bioluminescence resonance energy transfer (BRET), such as that described in Xu, et al., PROC. NATL. ACAD. SCI. USA, 96:151 (1999). Similar to a FRET assay, BRET is based on energy transfer from a bioluminescent donor to a fluorescent acceptor protein. However, a green fluorescent protein (GFP) is used as the acceptor molecule, eliminating the need for an excitation light source. Exemplary BRET assays include BRET and BRET$^2$ from Packard BioScience (Meriden, Conn.). It is understood that PTM and TRAF may be configured in the assay in any workable manner, such as alternatively labeling PTM or TRAF with GFP. It is further understood that inhibitors and enhancers of the PTM and TRAF interaction may be identified as described above for the FRET assay.

DELFIA® (dissociated enhanced lanthanide fluoroimmunoassay) is a solid-phase assay based on time-resolved fluorometry analysis of lanthanide chelates (see, for example, U.S. Pat. No. 4,565,790). For this type of assay, microwell plates are coated with a first protein (PTM-containing protein or TRAF). The binding partner (TRAF or PTM-containing protein, as the case may be) is conjugated to europium chelate or cryptate, and added to the plates. After suitable incubation, the plates are washed and a solution is added to dissociate europium ions from solid phase bound protein into solution, thereby forming highly fluorescent chelates with ligands present in the solution, after which the plates are read using a plate reader to detect emission at 615 nm.

Another assay that may be employed is a FlashPlate®-based assay (Packard Instrument Company, IL). This assay measures the ability of compounds to inhibit protein-protein interactions. FlashPlates are coated with a first protein (either TRAF or PTM-containing protein), then washed to remove excess protein. For the assay, compounds to be tested are incubated with the second protein (TRAF, if the plates are coated with PTM-containing protein, or PTM-containing protein if plates are boated TRAF), and $I^{125}$-labeled antibody against the second protein is added to the plates. After suitable incubation and washing, the amount of radioactivity bound is measured using a scintillation counter.

Further embodiments include the AlphaScreen™ assay (Packard Instrument. Company, Meriden, Conn.). AlphaScreen technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of PTM and TRAF), the singlet-state oxygen molecules reacts with chemiluminescent groups in the acceptor beads, which immediately transfer energy to fluorescent acceptors in the same bead. These fluorescent acceptors shift the emission wavelength to 520-620 nm, resulting in a detectable signal. Inhibitors of the interaction of PTM and TRAF will thus reduce the shift in emission wavelength, whereas enhancers of this interaction would increase it.

In one embodiment, a screening method of the present invention comprises the steps of forming a composition comprising a TRAF, a PTM-containing protein, and the test compound; assaying for the level of interaction of the TRAF and the PTM-containing protein; and comparing the level obtained in the presence of the test compound to that obtained in the absence of the test compound, such that if the level obtained differs, a compound that affects the interaction of the TRAF and the PTM-containing protein is identified. Preferably, at least one of the TRAF and the PTM-containing protein can be labeled with a detectable moiety. One of the TRAF and the PTM-containing protein can be soluble, and the other can be bound, although alternative assay formats are possible and well known. The test compound can be added to the composition after addition of the TRAF and the PTM-containing protein, before both proteins are added, or after one protein is added and before the other is added. The interaction of the TRAF with the PTM-containing protein that may be influenced by the test compound includes reciprocal binding of the TRAF and the PTM-containing protein. For example, a test compound may partially or completely inhibit binding of the TRAF to the PTM-containing protein. This partial or complete inhibition of binding can be measured in various ways, such as determining the binding constant in the presence and absence of the test compound. In other embodiments, the binding affinity and/or binding avidity between TRAF and PTM-containing protein may be measured with and without the test compound.

The above-described methods can be incorporated in high throughput test systems so that large numbers of test molecules can be screened within a short amount of time. The assays can be performed in a variety of formats, including protein-protein binding assays, biochemical screening assays, immunoassays, or cell-based assays. These assay formats are well known in the art. The screening assays of the present invention are amenable to screening of chemical libraries and are suitable for the identification of small molecule drug candidates, antibodies, peptides, peptidomimetics, and the like. Chemical libraries include commercially-available combinatorial chemistry compound libraries from companies such as, but not limited to, Sigma-Aldrich (St. Louis, Mo.), Arqule (Woburn, Mass.), Enzymed (Iowa City, Iowa), Maybridge Chemical Co. (Trevillett, Cornwall, UK), MDS Panlabs (Bothell, Wash.), Pharmacopeia (Princeton, N.J.), and Trega (San Diego, Calif.).

Moreover, combinations of screening assays can be used to find molecules that regulate the biological activity of TRAF/PTM interactions. In using combinations of various assays to screen for test compounds, it is understood that the assays described herein may be used in any suitable order and combination. For example, one embodiment may comprise first determining whether a test compound binds to TRAF or PTM or modulates the binding between TRAF and PTM by using an assay that is amenable to high throughput screening. Test compounds identified in this manner are then added to a biological assay to determine biological effects. By observing the effect that candidate molecules have on the interaction between PTM and TRAF in various binding assays, on PTM-mediated activity in biological function tests, or in cell based screens, molecules that are potential therapeutics because they can modulate the interaction between PTM and TRAF are identified. These molecules will be useful in treating or preventing disease or conditions with which PTM or TRAF are implicated.

RANK modulators can also be identified based on rational drug design. One goal of rational drug design is to produce structural analogs of biologically-active polypeptides or compounds with which they interact (e.g., agonists, antagonists, inhibitors, or binding partners). By creating such analogs, it is possible to fashion drugs which are more active or stable than the natural molecules, which have different susceptibility to alteration or which may affect the function of various other molecules. In one approach, one would generate a three-dimensional structure for PTM-containing protein (e.g., an endogenous RANK cytoplasmic domains or a fragment thereof) or TRAF. This could be accomplished by x-ray crystallograph, NMR, computer modeling, or by a combination of these approaches. An alternative approach, "alanine scan," involves the random replacement of residues throughout molecule with alanine, and the resulting affect on function determined.

It is also possible to isolate a PTM or TRAF specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically-active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using any method suitable for producing antibodies, using an antibody as the antigen.

In many cases, an inhibitor identified by the present invention can inhibit PTM-TRAF binding or consequential biological activity (e.g., osteoclastogenesis or bone resorption) by at least 30%, 40%, 50%, 60%, 70%, 80%, 90% or more. Similarly, a stimulator of the present invention can increase the PTM-TRAF binding or consequential biological activity by at least 20%; 30%, 40%, 50% or more. Those of ordinary kill in the art will recognize that RANK modulators with different levels of inhibition or enhancement may be useful for different applications (e.g., for treatment of different disease states).

RANK modulators of the present invention can be virtually any type of molecule, such as small molecules, peptide, peptide mimics, or antibodies. Exemplary antibodies amenable to the present invention include, but are not limited to, monoclonal antibodies, mono-specific antibodies, poly-specific antibodies, non-specific antibodies, humanized antibodies, human antibodies, single-chain antibodies, chimeric antibodies, synthetic antibodies, recombinant antibodies, hybrid antibodies, Fab, F(ab')$_2$, Fv, scFv, Fd, dAb, or biologically-active fragments thereof. In one embodiment, an antibody of the present invention includes two or more antigen-binding sites, each of which recognizes a different respective PTM or its corresponding TRAF protein. Binding of this antibody to these PTMs or their respective TRAFs inhibit two or more PTM-mediated RANK signaling pathways selected from the group consisting of PTM3-mediated RANK signaling pathway, PTM5-mediated RANK signaling pathway, and PTM6-mediated RANK signaling pathway. In one specific example, an antibody of the present invention can bind to at least two PTM motifs selected from PTM3, PTM5, and PTM6, and the binding affinity for each motif is at least $10^{-5}$ M$^{-1}$, $10^{-6}$ M$^{-1}$, $10^{-7}$ M$^{-1}$, $10^{-8}$ M$^{-1}$, $10^{-9}$ M$^{-1}$, or stronger.

The present invention further features pharmaceutical compositions comprising one or more RANK modulators identified according to the present invention. Each pharmaceutical composition is capable of modulating (e.g., inhibiting) at least two RANK-mediated pathways selected from the group consisting of PTM3-mediated RANK signaling pathway, PTM5-mediated RANK signaling pathway, and PTM6-mediated RANK signaling pathway. In one embodiment, a pharmaceutical composition of the present invention comprises one or more RANK modulators and is capable of modulating (e.g., inhibiting) the interactions of at least two different PTMs with their respective TRAF proteins, whereas each of the different PTMs is selected from PTM3, PTM5 or PTM6. In one specific example, a pharmaceutical composition of the present invention can modulate the interactions of PTM5 and PTM6 with their respective TRAF(s). In another specific example, a pharmaceutical composition of the present invention can modulate the interactions of PTM3 and PTM6 with their respective TRAF(s). In still another specific embodiment, a pharmaceutical composition of the present invention can modulate the interactions of PTM3 and PTM5 with their respective TRAF(s). Preferably, each PTM motif being modulated is a human PTM or comprises SEQ ID NOs:1-10.

A pharmaceutical composition of the present invention typically includes a therapeutically or prophylactically effective amount of one or more RANK modulators and a pharmaceutically-acceptable carrier. Suitable pharmaceutically-acceptable carriers include solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, that are compatible with pharmaceutical administration. The use of such media and agents for pharmaceutically-active substances is well known in the art. Supplementary agents can also be incorporated into the composition.

A pharmaceutical composition of the present invention can be formulated to be compatible with its intended route of administration. Examples of routes of administration include parenteral, intravenous, intradermal, subcutaneous, oral, inhalative, transdermal, rectal, transmucosal, topical, and systemic administration. In one example, the administration is carried out by an implant.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

A pharmaceutical composition of the present invention can be administered to a patient or animal in need thereof in a desired dosage. A suitable dosage may range, for example, from 5 mg to 100 mg, from 15 mg to 85 mg, from 30 mg to 70 mg, or from 40 mg to 60 mg. Dosages below 5 mg or above 100 mg can also be used. The pharmaceutical composition can be administered in one dose or multiple doses. The doses can be administered at intervals such as once daily, once weekly, or once monthly.

Toxicity and therapeutic efficacy of a RANK modulator can be determined by standard pharmaceutical procedures in cell culture or experimental animal models. For instance, the $LD_{50}$ (the dose lethal to 50% of the population) and the $ED_{50}$ (the dose therapeutically effective in 50% of the population) can be determined. The dose ratio between toxic and therapeutic effects is the therapeutic index, and can be expressed as the ratio $LD_{50}/ED_{50}$. In many cases, RANK modulators that exhibit large therapeutic indices are selected.

The data obtained from cell culture assays and animal studies can be used in formulating a range of dosages for use in humans. In one embodiment, the dosage is selected within a range of circulating concentrations that exhibit an $ED_{50}$ with little or no toxicity. The dosage may vary within this range depending upon the dosage form employed and the route of administration utilized.

The dosage regimen for the administration of a RANK modulator of the present invention can be determined by the attending physician based on various factors such as the action of the protein, the site of pathology, the severity of disease, the patient's age, sex and diet, the severity of any inflammation, time of administration, and other clinical factors. In one example, systemic or injectable administration is initiated at a dose which is minimally effective, and the dose is increased over a pre-selected time course until a positive effect is observed. Subsequently, incremental increases in dosage are made limiting to levels that produce a corresponding increase in effect while taking into account any adverse affects that may appear.

Progress of a treatment can be monitored by periodic assessment of disease progression. The progress can be monitored, for example, by X-rays, MRI or other imaging modalities, synovial fluid analysis, or clinical examination. As used herein, the terms "treat", "treating", and "treatment" includes curative, preventative (e.g., prophylactic) and palliative treatment.

Diseases amenable to the treatment of the present invention include, but are not limited to, osteoporosis, rheumatoid arthritis, cancer-induced bone lesions, T-cell or B-cell malignancies, or other cancers or bone disorders. In addition, familial expansile osteolysis and expansile skeletal hyperphosphatasia have been reported to be associated with abnormal intracellular accumulation of RANK, which leads to excessive NF-κB activity. See Hughes, et al., NAT. GENET., 24:45-48 (2000); and Whyte and Hughes, J. BONE MINER. RES., 17:26-29 (2002). Inhibition of the PTM-TRAF interactions by using a RANK modulator of the present invention will reduce RANK-mediated signaling activities, thereby alleviating the diseases caused by irregular activation of RANK-mediated pathways.

The following examples are offered by way of illustration, and not by way of limitation. Those skilled in the art will recognize that variations of the invention embodied in the examples can be made, especially in light of the teachings of the various references cited herein, the disclosures of which are incorporated by reference in their entirety.

EXAMPLES

Example 1

Experimental Procedures

Example 1 describes methods and materials employed in the following examples.

Chemicals and Reagents

Chemicals were purchased from Sigma (St. Louis, Mo.) unless indicated otherwise. Synthetic oligonucleotides were purchased from Sigma-Genosys (The Woodlands, Tex.). Blasticidin was from EMD Biosciences, Inc (San Diego, Calif.). Antibody against the external domain of mouse TNFR1 (for flow cytometry) (TNF-R1, sc-12746PE) was purchased from Santa Cruz Biotechnology, Inc (Santa Cruz, Calif.). Recombinant mouse TNFα (410-TRNC-050) was from R&D Systems (Minneapolis, Minn.). The following antibodies were purchased from Cell Signaling Technology, Inc (Beverly, Mass.): antibodies against IκBa (#9242), phospho-IκBa (#9241), p44/42ERK (#9102), phospho-p44/42ERK (#9101), JNK (#9252), phospho-JNK (#9251), p38 (#9212), phospho-p38 (#9211), Akt (#9272), phospho-Akt (#9271), AFX (#9472), phospho-AFX (#9471), phospho-GSK3α/β (#9331), GSK3β (#9332), phospho-FKHR/FKHRL1 (#9464), FKHR (#9462), phospho-BAD (#9297), and BAD (#9292).

Construction of TNFR1/RANK Chimeric cDNA

A chimeric cDNA comprising mouse TNFR1 external domain (from AA 1 to AA 210) linked in frame to the transmembrane and cytoplasmic domains of mouse RANK (AA 210 to AA 625) was constructed using standard molecular cloning techniques. The amino acid sequences of mouse TNFR1 and RANK genes have Entrez accession numbers NP_035739 (SEQ ID NO: 41) and NP_033425 (SEQ ID NO: 32), respectively. cDNA fragment encoding mouse TNFR1 external domain was amplified by RT-PCR using total RNA isolated from mouse bone marrow macrophages (BMMs) and a pair of primers containing XbaI sites. The TNFR1 cDNA fragment was then subcloned into pBluescript II SK+ cloning vector (Stratagene, La Jolla, Calif.) at XbaI site, resulting in a plasmid named SK-TNFR1. cDNA encoding the RANK transmembrane and cytoplasmic domains was also amplified by RT-PCR using total RNA from mouse BMMs with a forward primer containing SpeI site and a reverse primer containing BamHI site. The RANK cDNA fragment was then subcloned into SK-TNFR1 between SpeI and BamHI, giving rise to a plasmid named SK-TNFR1-RANK. The orientation and sequence of the chimeric cDNA was confirmed by sequencing.

Preparation of Retrovirus Encoding the Chimeric Receptors

The retrovirus vector pMX-puro (Onishi, et al., Mol. Cell Biol., 18:3871-3879 (1998)) and the Plat-E packaging cells (Morita, et. al., Gene Therapy, 7:1063-1066 (2000)) were used. The chimeric cDNA (TNFR1-RANK) from SK-TNFR1-RANK was subcloned into pMX-puro to generate plasmid construct named pMX-puro-TNFR1-RANK. Plat-E cells were cultured in DMEM with 10% heat-inactivated FBS, as described in Morita, et al. (supra). pMX-puro-TNFR1-RANK was transiently transfected into Plat-E cells using Lipofectamine Plus (Invitrogen, Carlsbad, Calif.). Virus supernatant was collected at 48, 72 and 96 h after transfection.

Culturing and Infection of Bone Marrow Macrophages (BMMs)

Bone marrow cells were isolated from long bones of 4-8 week old TNFR1$^{-/-}$R2$^{-/-}$ double knockout mice (The Jackson Laboratory, Bar Harbor, Me.) or wild-type mice (Harlan Industries, Indianapolis, Ind.), as described in Feng, et al., J. Clin. Invest., 107:1137-1144 (2001). BMMs were prepared by culturing isolated bone marrow cells in α-MEM containing 10% heat-inactivated FBS in the presence of 0.1 volume of culture supernatant of M-CSF-producing cells for 2 days as previously described in Takeshita, et al., J. Bone Miner. Res., 15: 1477-1488 (2000). Cells were then infected with virus for 24 hours in the presence of 0.1 volume of culture supernatant of M-CSF-producing cells and 8 µg/ml polybrene. Cells were further cultured in the presence of M-CSF and 2 µg/ml puromycin for selection and expansion of transduced cells. Selected cells were subsequently used for various studies.

In Vitro Osteoclastogenesis Assays and Bone Resorption Assay

Retrovirally-infected BMMs were cultured in 24-well tissue culture plates (1×10$^5$ cells/well) in α-MEM containing 10% heat-inactivated FBS in the presence of 0.01 volume of culture supernatant of M-CSF-producing cells (final M-CSF concentration is 22 ng/ml) and 100 ng of GST-RANKL (Lam, et al., J. Clin. Invest., 106:1481-1488 (2000)). In osteoclastogenesis assays involving the use of the chimeric receptor, TNFα was added at concentrations as indicated in individual assays. Osteoclast began to form on day 3 and cultures were stained for tartrate-resistant acid phosphatase (TRAP) activity on day 5 using a commercial kit (Sigma, 387-A). In other assays, the cultures were treated with different factors as indicated in individual assays after osteoclast formation, and then continued for 14 more hours. The cultures were then stained for TRAP activity. Survived osteoclasts were determined as those cells with strong TRAP activity, more than 3 nuclei and intact plasma membrane.

To perform bone resorption assays, osteoclasts were generated on whale dentin slices from infected or uninfected BMMs as described above. Dentin slices were harvested at day 9. Cells were removed from the dentin slices with 0.25 M ammonium hydroxide and mechanical agitation. Dentin slices were then subjected to scanning electron microscopy (SEM).

Flow Cytometric Analysis

Infected BMMs (up to 1×10$^6$ cells) were suspended in 200 µl PBS/Azide. Cells were then blocked with 1 µg 2.4G2 antibody (Unkeless, J. Exp. Med., 150:580-596 (1979)) for 30 min on ice. Under dim light, 20 µl of TNFR1 antibody conjugated with phycoerythrin (Santa Cruz, Calif., sc-12746PE) or control IgG was added to the cell suspension and cells were incubated on ice for 30 min. Cells were washed twice with 1 ml cold PBS/Azide and resuspended in 300 µl cold PBS/Azide. 200 µl cold 0.5% paraformaldehyde solution was added to fix the cells. Flow cytometric analysis was performed using a Becton-Dickinson FACSan (Becton-Dickinson Immunocytometry Systems, Mountain View, Calif.).

Mutagenesis

Mutations were generated in SK-TNFR1-RANK using the QuickChange™ Site-directed Mutagenesis Kit (Stratagene). To mutate the six putative TRAF-binding motifs (PTM), the following oligonucleotides were used. For PTM 1, 5'-GTGT-GTGAAGGTGTCGTAGTATTGTCTCTG-GACGACAAGATGGTTCC-3' (SEQ ID NO:11) and 5'-GGAACCATCTTGTCGTCCAGAGA-CAATACGACACCTTCACACAC-3' (SEQ ID NO:12). For PTM2, 5'-GAGTACACGGACCGGCTCACGAAGCT-TACGA CTGGTTCACTG-3' (SEQ ID NO:13) and 5'-CAGTGAACCAGTCGTAAGGTTCGTG AGCCGGTC-CGTGTACTC-3' (SEQ ID NO:14). For PTM3, 5'-GCAAATCTATACC CCCATGGAACGACCTCCTG-GAAGTGGGG-3' (SEQ ID NO:15) and 5'-CCCCAC TTC-CAGGAGGTCGTTCCATAGGGGTATAGATTTGC-3' (SEQ ID NO:16). For PTM4, GACATCATCGTGGT-GTTTCTCACCAACTCCACGAACGACGGC-CCGGGTTC-3' (SEQ ID NO:17) and 5'-GGAACCCGGGC-CGTCGTTCGTGGAGTTGGTGAGAA ACAGCACGATGATGTC-3' (SEQ ID NO:18). For PTM5, 5'-CCCGTGGGCCGC CTTCTGAACGACGACTCGCTG-GCACAC-3' (SEQ ID NO:19) and 5'-GTGTG CCAGC-GAGTCGTCGTTCAGAAGGCGGCCCACGGG-3' (SEQ ID NO:20). For PTM6, 5'-GGGACATCGCGGCTGCT-GAACGACAACGCTGGGGCGCAG-3' (SEQ ID NO:21) and 5'-CTGCGCCCCAGTTGTCGTTCAGCAGC-CGCGATGTCCC-3' (SEQ ID NO:22). The intended mutations are indicated by lower case letters in these oligonucleotides. The mutated sites were confirmed by sequencing, and other regions in the chimeric cDNA were sequenced to confirm that no mutations were introduced by PCR amplification during the mutagenesis. The mutant chimeric cDNAs were then subcloned into pMX-puro plasmids as described above for virus preparation.

Western Analysis

BMMs infected with retrovirus or control BMMs (uninfected) were cultured in serum-free α-MEM in the absence of M-CSF for 16 h before treatment with RANKL or TNFα for various times as indicated in individual experiments. For assays involving osteoclasts, BMMs were treated with M-CSF (22 ng/ml) and RANKL (100 ng/ml) for 4 days to stimulate osteoclast formation. After osteoclasts were formed, the cultures were then treated with PBS or RANKL for 2 or 5 hours. Cells were washed twice with ice-cold phosphate-buffered saline (PBS) and then lysed in buffer containing 20 mM Tris, pH 7.5, 150 mM NaCl, 1 mM EDTA, 1 mM EGTA, 1% Triton X-100, 2.5 mM sodium pyrophosphate, 1 mM (3-glycerophosphate, 1 mM $Na_3VO_4$, 1 mM NaF, and 1× protease inhibitor cocktail 1 (Sigma, P-2850) and 1× protease inhibitor cocktail 2 (Sigma, P-5726). 40 µg of cell lysates were boiled in the presence of SDS sample buffer (0.5 M Tris-HCl, pH 6.8, 10% (w/v) SDS, 10% glycerol, 0.05% (w/v) bromophenol blue) for 5 min and loaded for electrophoresis on 10% SDS-PAGE. Proteins were transferred to nitrocellulose membranes (Cat#162-0147) from Bio-Rad (Hercules, Calif.) using a semi-dry blotter (Bio-Rad). Membranes were blocked in blocking solution (5% non-fat dry milk in TBS containing 0.1% Tween 20) for 1 h to prevent nonspecific binding and then washed three times with TBS-T (TBS containing 0.1% Tween 20). Membranes were incubated primary antibodies in TBS-T containing 5% bovine albumin (Sigma, Cat#A-7030) overnight at 4° C. Next day, membranes were then washed three times with TBS-T and incubated with secondary antibody in TBS-T containing 5% non-fat dry milk for 1 h. Membranes were washed extensively and enhanced chemiluminescence (ECL) detection assay was performed using SuperSignal West Dura kit from Pierce (Rockford, Ill.).

Sequence Analysis

Sequence analysis was performed using the Genetic Computer Group (Madison, Wis.) sequence analysis software.

Example 2

Construction of a Chimeric Receptor Capable of Mediating Osteoclast Formation and Function To delineate functional motifs in the RANK cytoplasmic domain mediating osteoclast differentiation and function, a chimeric receptor comprising mouse TNFR1 external domain (AA 1 to AA 210) linked to the transmembrane and intracellular domains of mouse RANK (AA 210 to AA 625) was developed (FIG. 1B). Given that both TNFR1 and RANK belong to the same family of the cytokines and that they are both activated by trimerization (FIGS. 1A and 1B), the TNFα-induced trimerization of the chimeric receptor is postulated to be sufficient to activate RANK intracellular signaling pathways required for the osteoclast formation and/or function (FIG. 1B).

Figure 2:
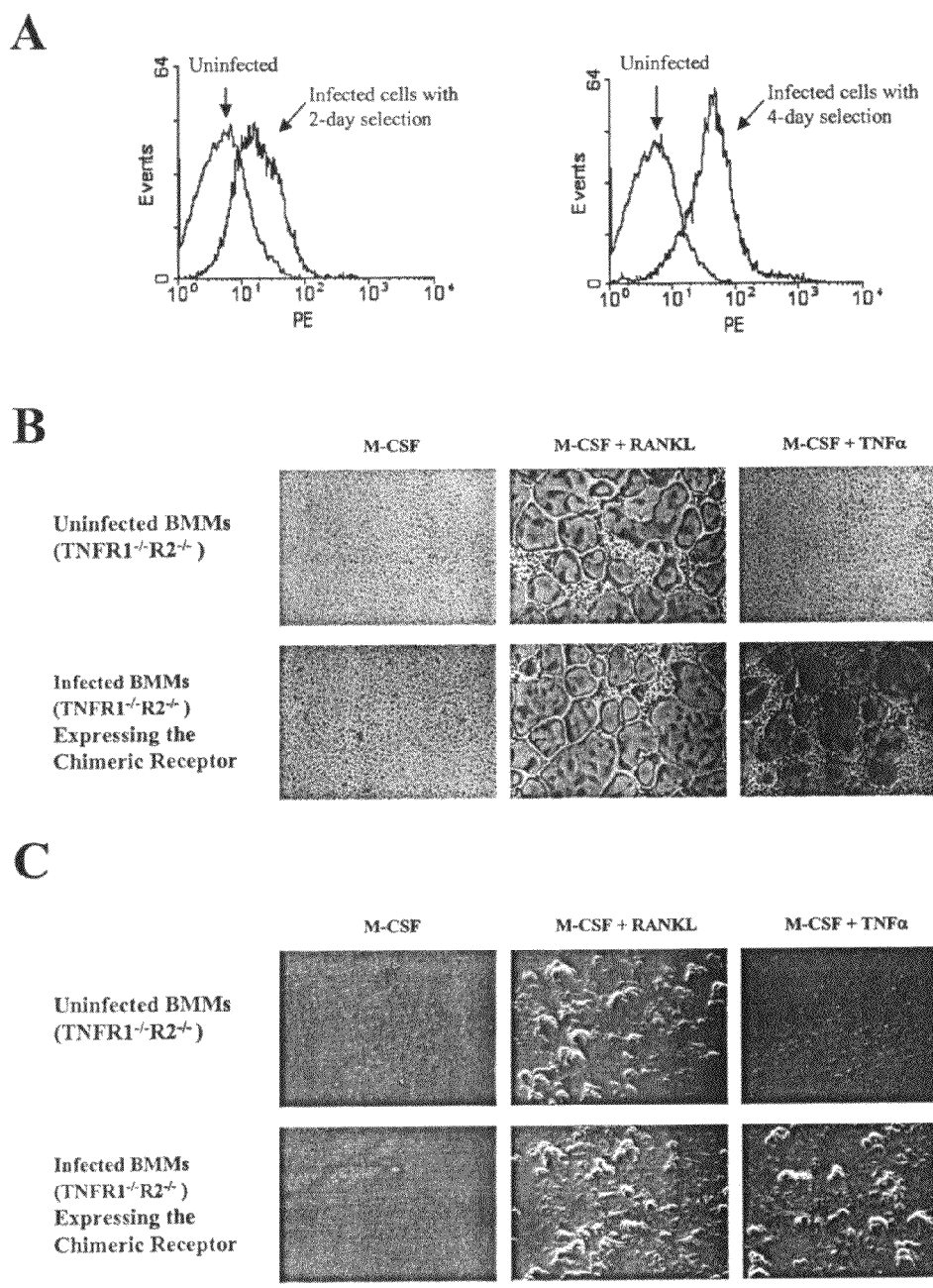
FIG. 2A depicts flow cytometric analysis showing the surface expression of the chimeric receptors of FIG. 1B on infected bone marrow macrophages (BMMs). BMMs isolated from TNFR1$^{-/-}$ & 2$^{-/-}$ mice were infected with retrovirus encoding the chimeric receptor for 24 hours. Infected cells were cultured in the presence of puromycin (2 μg/ml) for 2 or 4 days to select for the chimera expression-positive cells. The surface expression of the chimera was determined by flow cytometric analysis using TNFR1 antibody conjugated with phycoerythrin. Uninfected BMMs were used as control.
FIG. 2B shows the results of osteoclastogenesis assays with the chimeric receptor of FIG. 1B. TNFR1$^{-/-}$ & 2$^{-/-}$ BMMs were either uninfected or infected with virus encoding the chimeric receptor. Infected cells were then selected with puromycin for 2 days. Uninfected BMMs or infected BMMs were then treated with M-CSF alone (22 ng/ml), M-CSF (22 ng/ml) plus RANKL (100 ng/ml), or M-CSF (22 ng/ml) plus TNFα (100 ng/ml). Osteoclasts began to form at day 3 and the cultures were stained for TRAP activity at day 6.
FIG. 2C demonstrates the results of bone resorption assays. Uninfected or infected BMMs as described in (B) were plated on dentin slices and the cultures were treated with M-CSF alone (22 ng/ml), M-CSF (22 ng/ml) plus RANKL (100 ng/ml), or M-CSF (22 ng/ml) plus TNFα (100 ng/ml). After osteoclasts formed, the cultures were continued for 5 more days to allow the cells to resorb bone. The dentin slices were harvested and subjected to scanning electron microscopy (SEM) analysis.

To determine whether the chimeric receptor is capable of mediating osteoclast formation and function, the above-described chimeric receptor was expressed in primary BMMs using a retroviral system (FIG. 2). Given that TNFα is also implicated in osteoclast formation and function, BMMs from TNFR1 and R2 double knockout mice ($TNFR1^{-/-}R2^{-/-}$) were used to eliminate the possibility of signaling through TNF receptors. BMMs derived from $TNFR1^{-/-}R2^{-/-}$ mice were infected with the retrovirus encoding the chimeric receptor and the cells expressing the chimera were selected with 1 µg/ml puromycin for 2 or 4 days. Flow cytometric analysis with antibody against the external domain of TNFR1 demonstrated that the chimera was not only expressed on the cell surface, but also the surface expression levels of the chimera were increased with the selection time (FIG. 2A).

To determine whether the chimeric receptor is capable of mediating osteoclast differentiation, infected BMMs expressing the chimera were treated with M-CSF (22 ng/ml), M-CSF (22 ng/ml) plus RANKL (100 ng/ml), or M-CSF (22 ng/ml) plus TNFα (10 ng/ml) (FIG. 2B). While infected BMMs treated with M-CSF alone remained in macrophage lineage, those treated with M-CSF and RANKL formed osteoclasts, indicating that the endogenous RANK in the infected cells is functional (FIG. 2B). When infected BMMs were treated with M-CSF and TNFα, they also formed osteoclasts, confirming that the chimeric receptor is working (FIG. 2B). As a negative control, uninfected BMMs failed to form osteoclasts in response to M-CSF and TNFα treatment (FIG. 2B). Notably, the infected cell culture treated with M-CSF alone also contained few TRAP-positive cells (FIG. 2B). This might be a result of over-expression of the chimera in a few BMMs, since over-expression of TNFR family members can lead to the self-activation of their signaling pathways. Functionally, these TRAP-positive cells may not be regarded as osteoclasts because the high power view of the culture indicates that they were still mononuclear. In addition, as shown in FIG. 2C, these TRAP-positive mononuclear cells failed to form any pits in the resorption assays. Thus, the formation of few TRAP-positive mononuclear cells in this culture will not undermine the chimera's potential as a tool to study RANK signaling. In FIG. 2B, TNFα at the concentration of 10 ng/ml was used. Subsequent studies showed that lower TNFα concentrations (as low as 1 ng/ml) were still able to mediate osteoclast formation.

To examine whether osteoclasts generated using the chimera strategy are capable of resorbing bone, bone resorption assays were performed (FIG. 2C). Osteoclasts generated using the chimera approach resorbed bone as efficiently as those formed using the endogenous RANK (FIG. 2C). Taken together, these data indicate that a chimera comprising TNFR1 external domain linked to the transmembrane and cytoplasmic domains of RANK is able to mediate osteoclast formation and function, using TNFα as a surrogate of RANKL. This chimera can serve as a useful tool for studying RANK signaling in osteoclast differentiation and function.

Example 3

Figure 3:
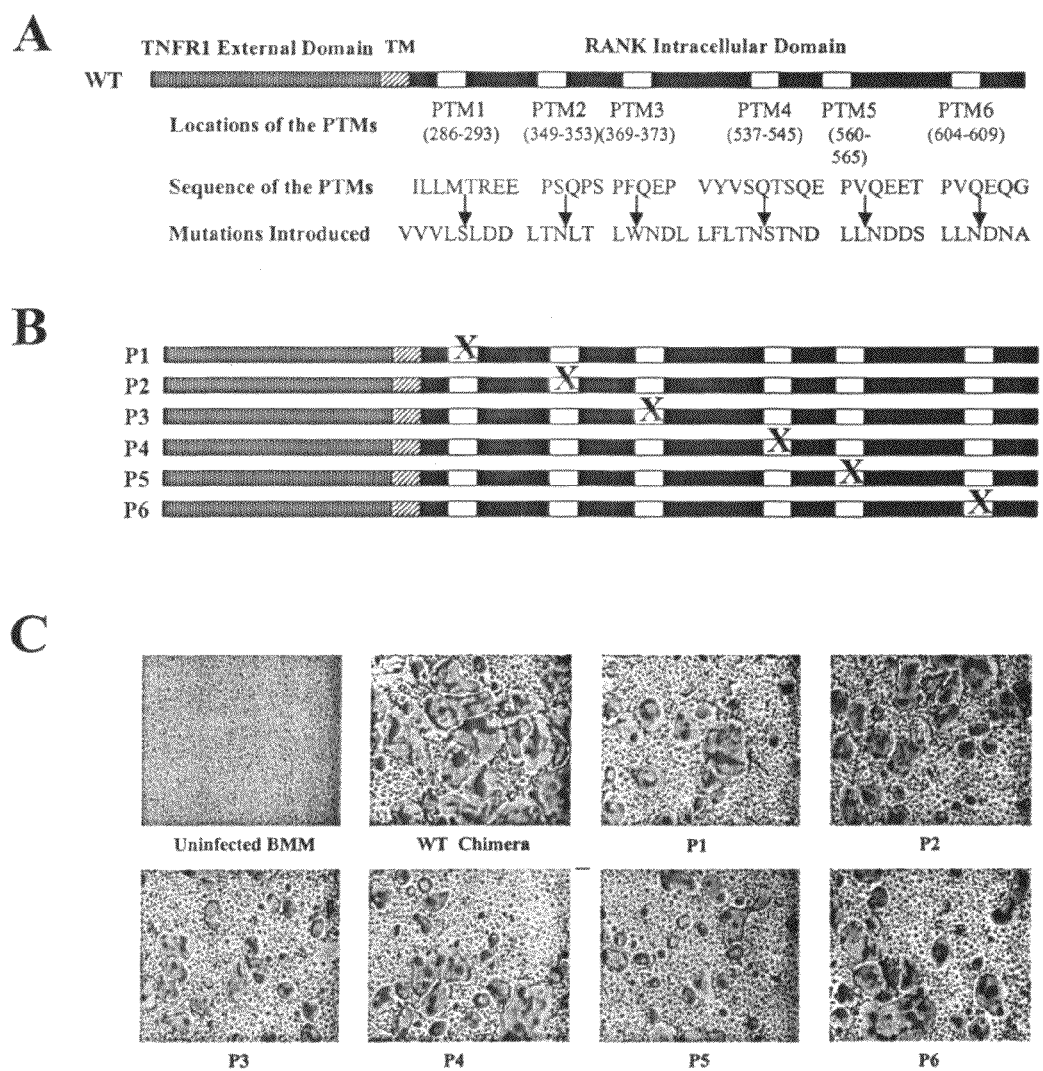
FIG. 3A is a schematic diagram showing six putative TRAF-binding motifs (PTMs). The sequence and location of each PTM (SEQ ID NOS 23, 24, 1, 25, 2 and 3, respectively, in order of appearance), as well as the sequence of the corresponding mutant (SEQ ID NOS 26-31, respectively, in order of appearance), are also provided.
FIG. 3B schematically depicts six mutant chimeric receptors (designated as P1, P2, P3, P4, P5, and P6, respectively). These mutants have only a single PTM mutated. The sequences of these mutations are shown in FIG. 3A.
FIG. 3C illustrates the results of osteoclastogenesis assays with P1, P2, P3, P4, P5, and P6, respectively. The assays were performed as described in FIG. 2B. Infected BMMs were treated with M-CSF (22 ng/ml) and TNFα (2 ng/ml).

Multiple RANK Cytoplasmic Motifs Are Involved in Osteoclast Formation and Function The chimeric receptor approach described in Example 2 was used to elucidate RANK cytoplasmic motifs that mediate osteoclast formation and function. RANK cytoplasmic domain contains six putative TRAF-binding motifs (PTM) that have been proposed to be able to initiate RANK signaling: PTM1, $ILLMTREE^{286-293}$ (SEQ ID NO:23); PTM2, $PSQPS^{349-353}$ (SEQ ID NO:24); PTM3, $PFQEP^{369-373}$ ((SEQ ID NO:1); PTM4, $VYVSQTSQE^{537-545}$ (SEQ ID NO:25); PTM5, $PVQEET^{559-564}$ (SEQ ID NO:2); PTM6, $PVQEQG^{604-609}$ (SEQ ID NO:3). As shown in FIG. 3A, these PTMs were mutated to VVVLSLDD (SEQ ID NO:26), LTNLT (SEQ ID NO:27), LWNDL (SEQ ID NO:28), LFLT-NSTND (SEQ ID NO:29), LLNDDS (SEQ ID NO:30) and LLNDNA (SEQ ID NO:31), respectively. These mutants were employed to investigate the role of the PTMs in osteoclast formation and function. The location and sequence of each PTM as well as the mutations introduced in these PTMs are highlighted in FIG. 3A. To minimize the potential effect of the point mutations on the 3-dimensional structure of the RANK intracellular domain, each amino acid in a PTM was mutated to an amino acid with similar chemical characteristics (e.g., similar chemical structure, polarity and charge).

FIG. 3B shows schematic structures of 6 mutant chimeric receptors constructed (named P1, P2, P3, P4, P5, and P6). Each mutant has one PTM mutated according to FIG. 3A (labeled with "X"). These mutant chimeric constructs were then used to perform the osteoclastogenesis assay (FIG. 3C). The result indicated that all six mutants exhibited no significant difference in their capacity to mediate osteoclast formation compared with the wild-type (WT) chimera (the one with no mutation in RANK cytoplasmic domain) (FIG. 3C). The assay was independently repeated 3 times and the same result was obtained. These results raised at least two possibilities: (a) none of the 6 PTMs plays a functional role in osteoclast formation; or (b) some of the PTMs are functionally redundant in mediating osteoclast formation.

Figure 4:
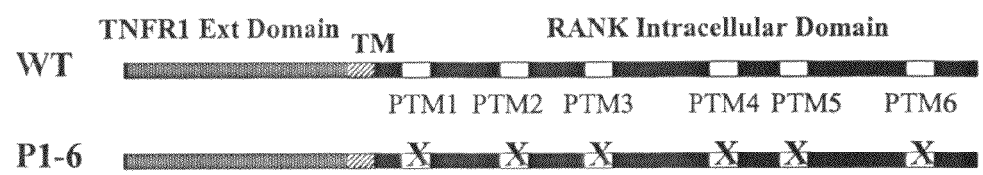
FIG. 4A is a schematic diagram of the constructed mutant chimeric receptors with all six. PTMs mutated (designated as P1-6).
FIG. 4B shows the results of osteoclastogenesis assays with P1-6. The assays were performed as described in FIG. 2B. Infected BMMs were treated either with 22 ng/ml of M-CSF plus 5 ng/ml of TNFα (top panel), or with 22 ng/ml of M-CSF plus 10 ng/ml of TNFα (bottom panel).
Figure 4:
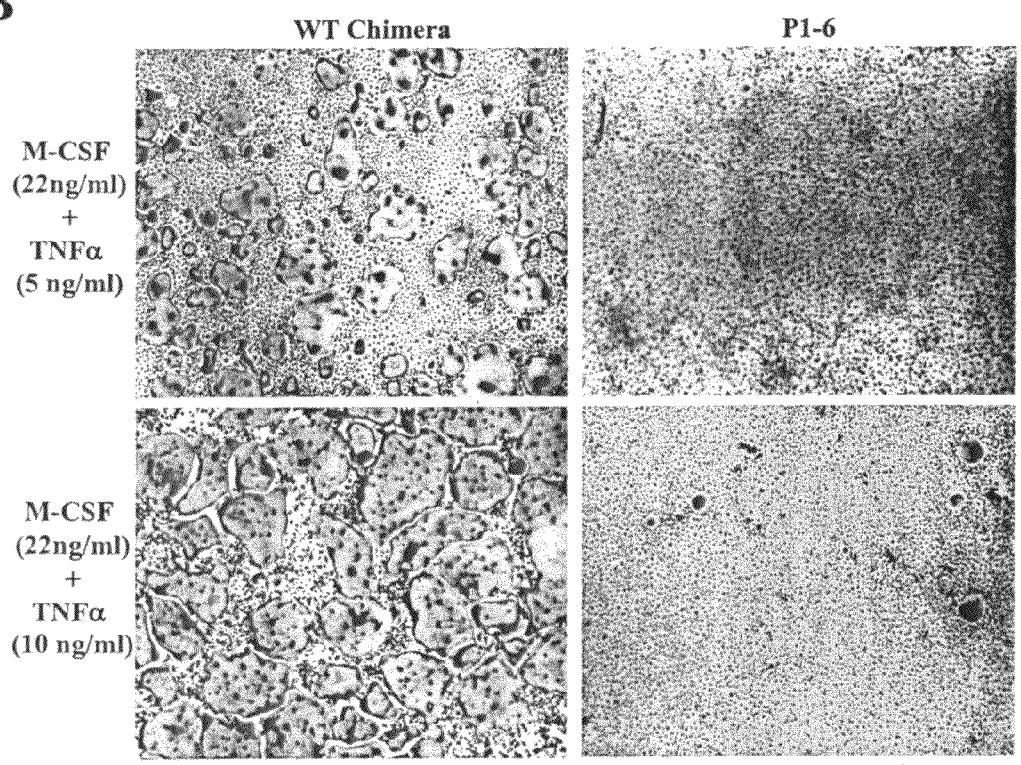

To address the issue, a mutant (P1-6) was generated, in which all six PTMs are mutated according to FIG. 3A (FIG. 4A). Viruses encoding P1-6 mutant or the wild-type chimera were prepared. Flow cytometric analysis showed that P1-6 mutant and the wild-type chimeras were expressed at similar levels on cell surface of BMMs infected with these viruses (data not shown). As shown in FIG. 4B, when infected cells were treated with 22 ng M-CSF and 5 ng TNFα, the wild-type chimera is capable of mediating osteoclast formation but P1-6 failed to do so (top panels, FIG. 4B). These data indicate that some of the sites are functionally redundant. Moreover, when 10 ng/ml TNFα was used for osteoclastogenesis assay, P1-6 resulted in a few TRAP positive cells (right bottom panel, FIG. 4B). This may be due to the possibility that the introduced mutations are not able to completely block the binding of downstream signaling molecules such as TRAF proteins. Taken together, these two sets of data indicate that some of the PTMs are functionally redundant in mediating osteoclast formation.

Example 4

Figure 5:
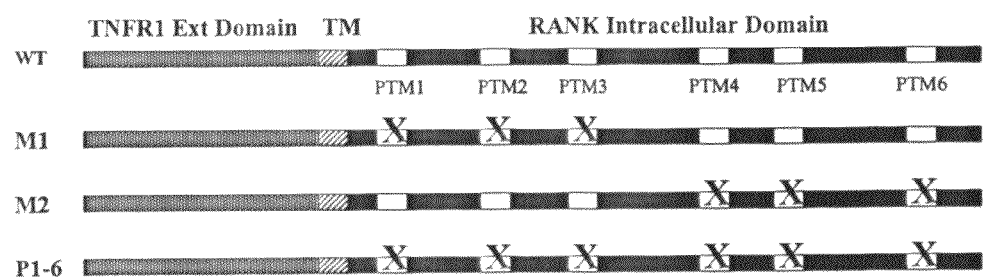
FIG. 5A is a schematic diagram of two mutant chimeric receptors with three PTMs mutated (designated as M1 and M2).
FIG. 5B demonstrates the results of osteoclastogenesis assays with M1 and M2. The assays were performed as described in FIG. 2B. Infected BMMs were treated with 22 ng/ml of M-CSF plus 5 ng/ml of TNFα.
Figure 5:
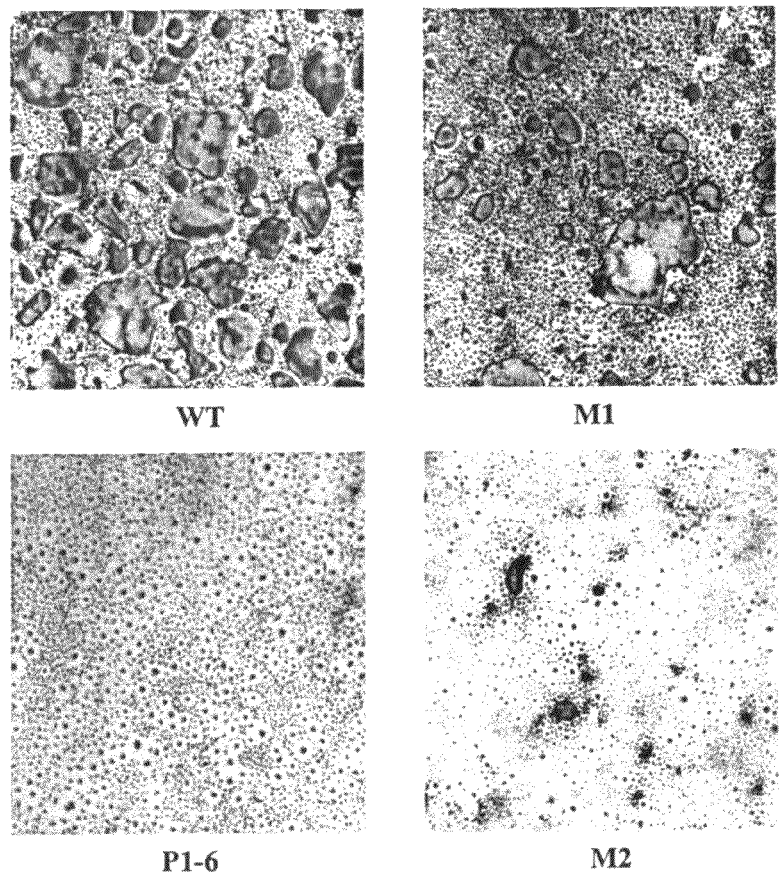

Identification of Three Functional RANK Motifs Mediating Osteoclast Differentiation and Function To identify the functional RANK cytoplasmic motifs, two mutant chimeric receptors were generated—namely, M1 and M2 (FIG. 5A). In M1, PTMs 1, 2 and 3 are mutated, while in M2, PTMs 4, 5 and 6 are mutated. Each PTM is mutated according to FIG. 3A. When M1 and M2 were used to repeat the osteoclastogenesis assays, both mutants formed osteoclasts (FIG. 5B), suggesting that some of the three non-mutated PTMs in both M1 and M2 are functional. Given that M1 showed a higher capacity to form osteoclasts than M2 (FIG. 5B), implying that more than one PTM among the three non-mutated PTMs in M1 (PTMs 4, 5 and 6) are probably capable of mediating osteoclast formation.

Figure 6A:
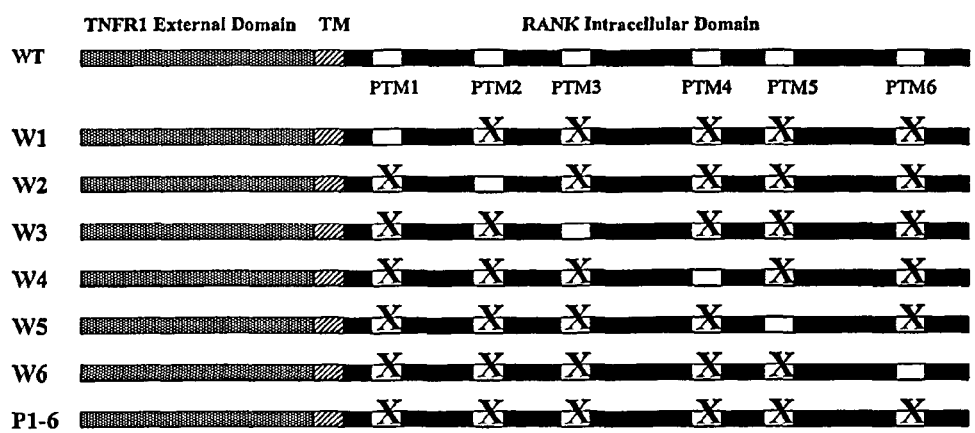
FIG. 6A schematically illustrates six mutant chimeric receptors that contain mutation in all PTMs except one (designated as W1, W2, W3, W4, W5 and W6, respectively).
Figure 6B:
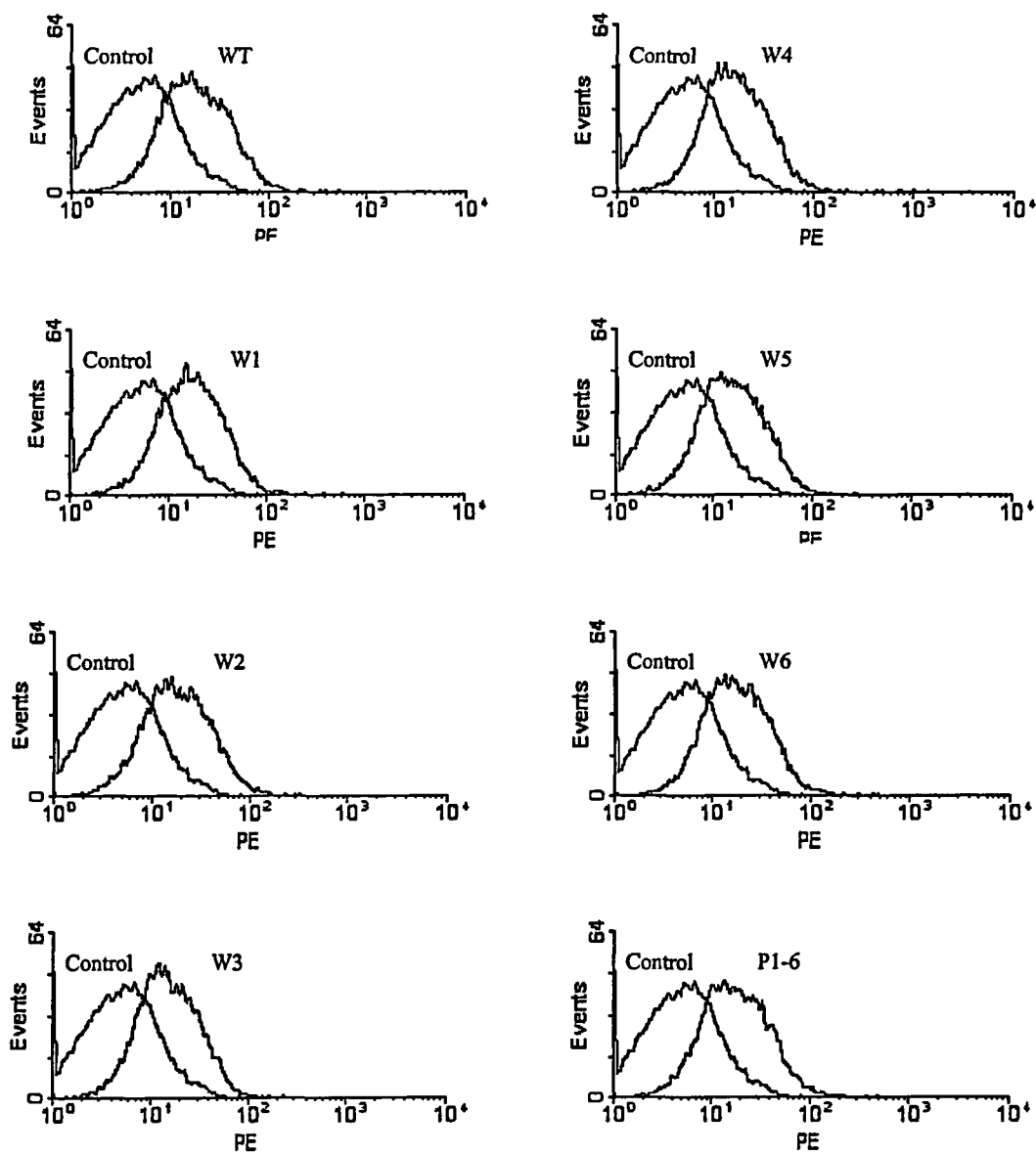
FIG. 6B describes flow cytometric analysis showing the surface expression of the chimeras on the BMMs infected with retrovirus encoding W1, W2, W3, W4, W5 and W6, respectively. The assay was performed as described in FIG. 2A.
Figure 6C:
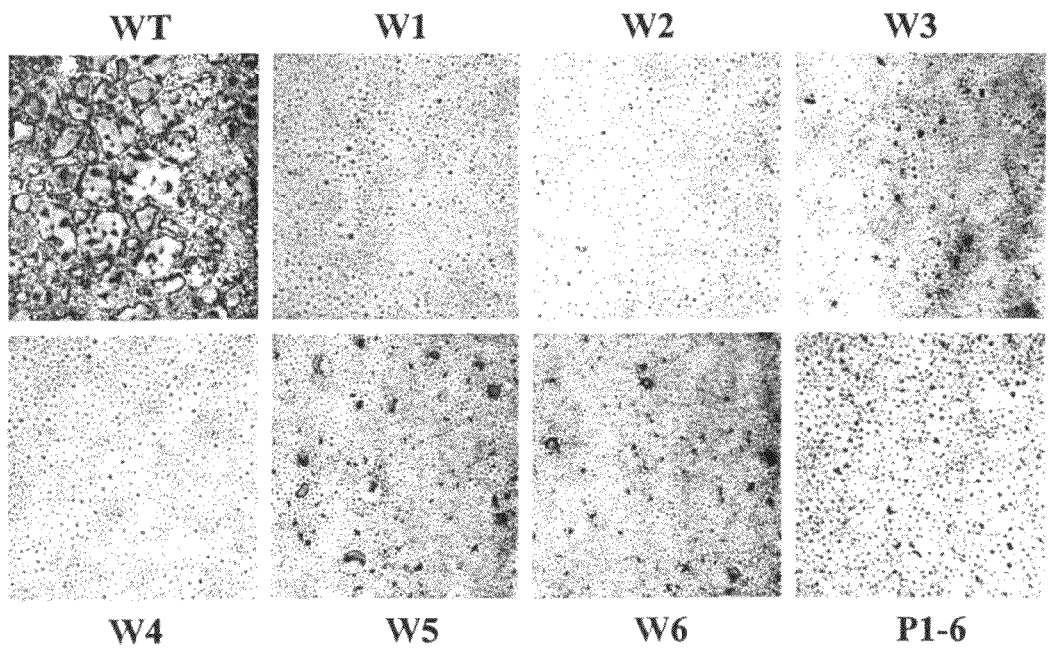
FIG. 6C illustrates the results of osteoclastogenesis assays with W1, W2, W3, W4, W5 and W6, respectively. The assays were performed as described in FIG. 2B. Infected BMMs were treated with 22 ng/ml of M-CSF plus 5 ng/ml of TNFα.
Figure 6D:
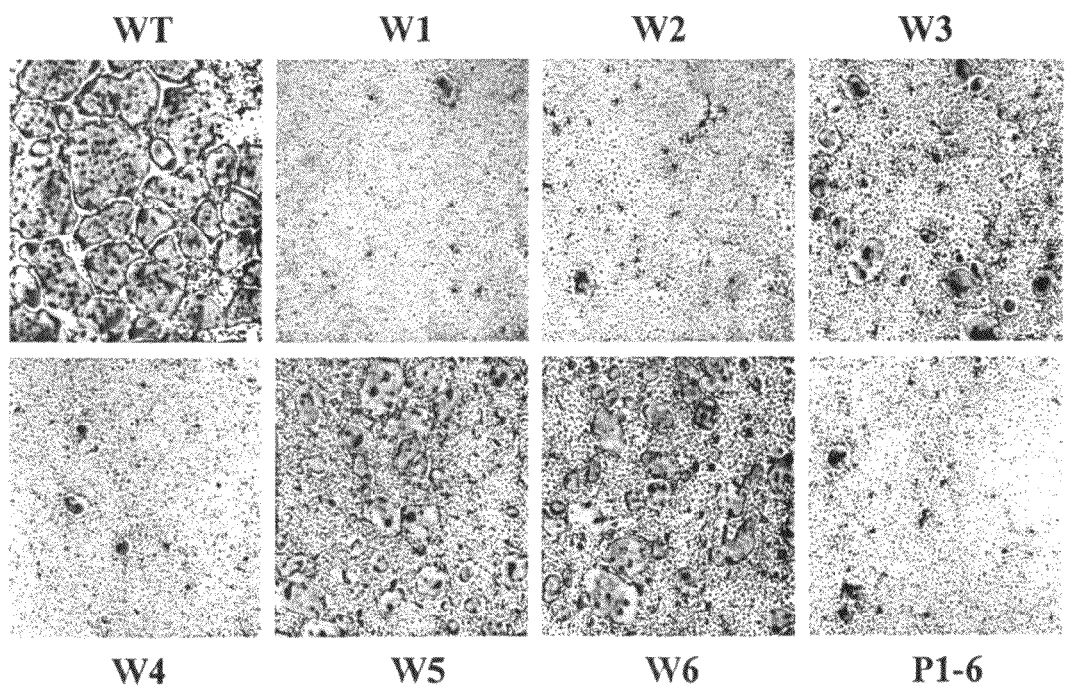
FIG. 6D depicts the results of osteoclastogenesis assays similar to those shown in FIG. 6C but with a higher dose of TNFα (10 ng/ml). The dose of M-CSF remained the same (22 ng/ml).

Based on the above data, six more mutants (W1, W2, W3, W4, W5 and W6) were prepared (FIG. 6A). In each of these mutants, only one PTM is not mutated, and each PTM is mutated according to FIG. 3A. BMMs infected with virus encoding these mutant chimeras were analyzed by flow cytometric analysis to confirm that all mutant chimeras were expressed at similar levels on cell surface (FIG. 6B). The mutant chimeras W1-W6 were then used to perform the osteoclastogenesis experiment with 22 ng/ml M-CSF and 5 ng/ml TNFα (FIG. 6C). Under these conditions, while W1, W2 and W4 failed to form TRAP-positive cells, W3, W5 and W6 were capable of forming some TRAP-positive cells (FIG. 6C), indicating that PTM3, PTM5, and PTM6 are functional sites. The osteoclastogenesis assay was repeated with higher TNFα concentrations (10 ng/ml). As shown in FIG. 6D, while W1, W2 and W4 gave rise to a culture similar to P1-6 culture, W3, W5 and W6 formed much more and bigger osteoclasts than P1-6 mutant. These data demonstrated that PTM3, PTM5, and PTM6 are functional RANK motifs in mediating osteoclast formation. Moreover, both sets of the assays suggested that PTM5 and PTM6 might be more potent than PTM3 in mediating osteoclast differentiation (FIGS. 6C and 6D).

Figure 7:
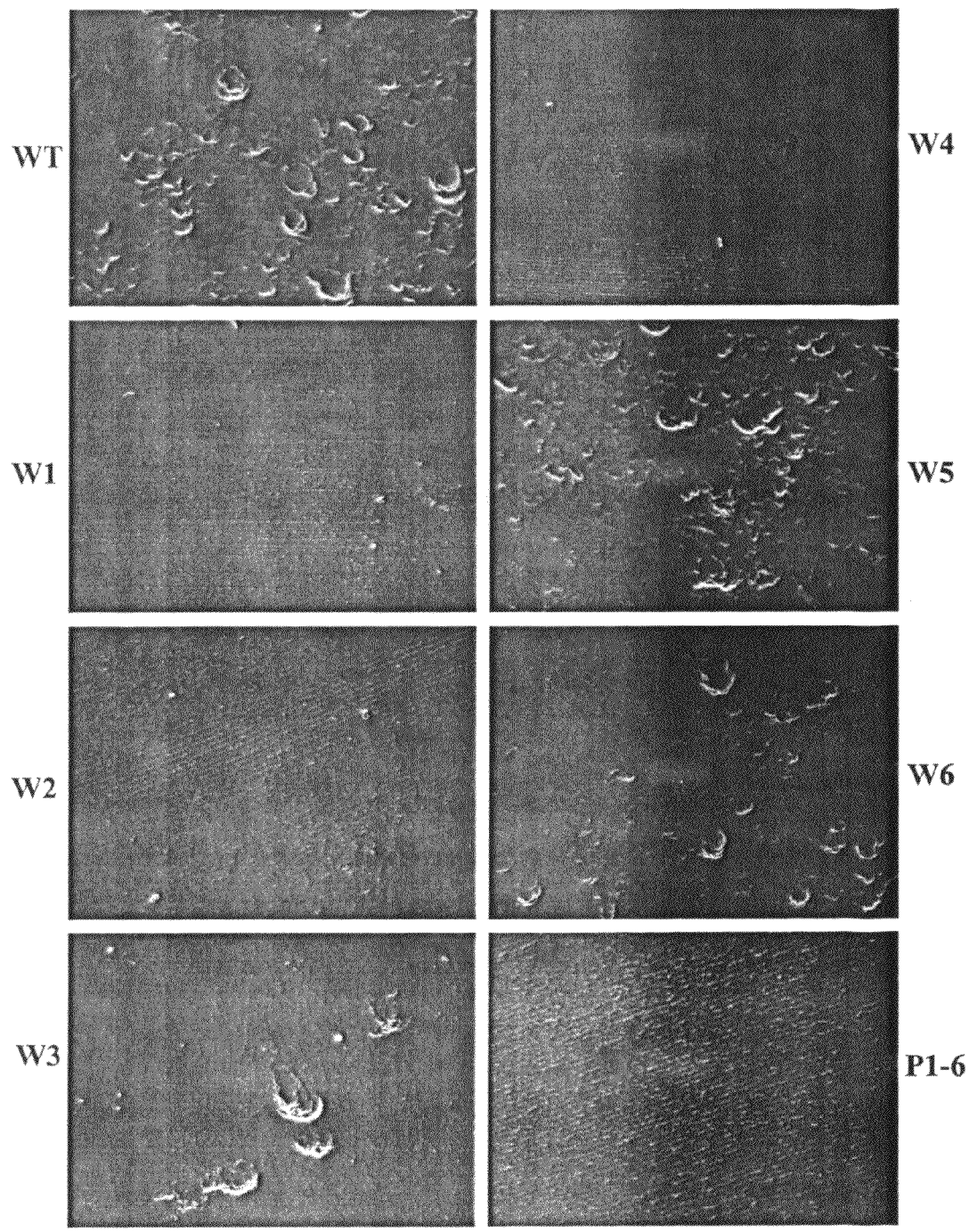
FIG. 7 shows bone resorption assays with W1, W2, W3, W4, W5 and W6, respectively. The resorption assays were performed as described in FIG. 2C. Infected BMMs were treated with M-CSF (22 ng/ml) and TNFα (5 ng/ml). Bone resorption pits from SEM are viewed at 100× magnifications.

To determine whether PTM3, PTM5, and PTM6 are able to mediate bone resorption, bone resorption assays were performed with BMMs infected with virus encoding the wild-type chimera, W1, W2, W3, W4, W5, W6 or P1-6 (FIG. 7). In this bone resorption assay, osteoclasts were generated in the presence of 22 ng/ml M-CSF and 5 ng/ml TNFα. No bone resorption pits were detected from the W1, W2, W4 and P1-6 since these mutants were not able to mediate osteoclast differentiation under the condition (22 ng/ml M-CSF and 5 ng/ml TNFα) (FIG. 6C). Dentin slices from the wild-type chimera, W3, W5 and W6 cultures showed resorption activities (FIG. 7), revealing that the three RANK motifs (PTM3, PTM5, and PTM6) are also capable of activating osteoclast bone resorption. Moreover, W3 gave rise to fewer bone resorption pits than W5 and W6, which is consistent with the osteoclastogenesis assay showing that W3 is less potent in modulating osteoclast differentiation than W5 and W6 (FIGS. 6C and 6D).

Example 5

Identification of Signaling Pathways Activated by Three Functional RANK Motifs

RANK mediates osteoclast formation and/or function by activating various intracellular signaling pathways including NF-κB, JNK, ERK and p38. This example investigated whether PTM3, PTM5, and PTM6 motifs are implicated in activation of these signaling pathways by performing Western analysis with antibodies against phosphorylated IκB, JNK, ERK or p38, as previously described in Wei, et al., J. BIOL. CHEM., 277:6622-6630 (2002).

Figure 8:
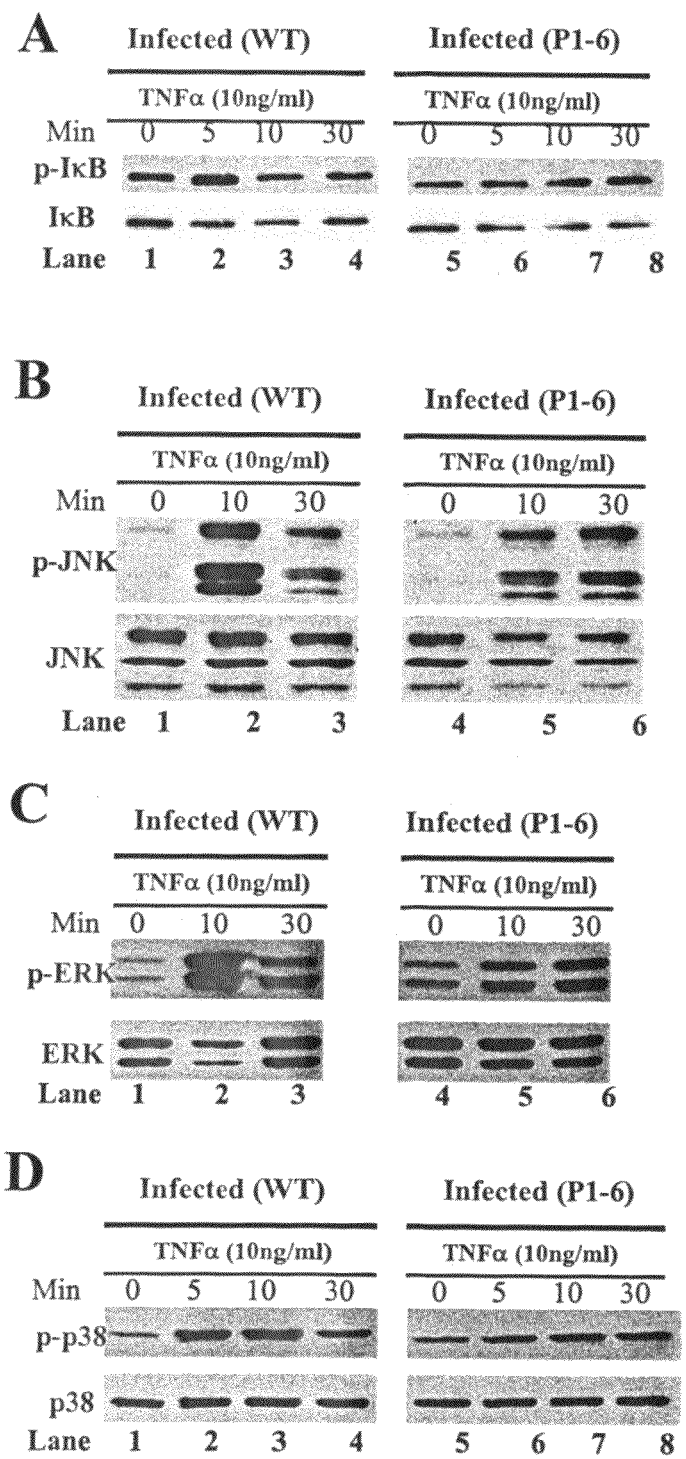
FIG. 8A shows that mutation of all PTMs blocks the activation of IκB/NF-κB pathway. Activation of IκB/NF-κB pathway by the wild-type chimera and P1-6 was assessed by detecting phosphorylation of IκB using Western analysis with antibodies against phospho-IκB (p-IκB). Immunoblots were stripped and then reprobed with antibodies against IκB as loading controls. Min: minute. WT: wild-type chimera.
FIG. 8B depicts that mutation of all PTMs blocks the activation of JNK pathway. Activation of JNK pathway by the wild-type chimera and P1-6 was assessed by detecting phosphorylation of JNK using Western analysis with antibodies against phospho-JNK (p-JNK). Immunoblots were stripped and then reprobed with antibodies against JNK as loading controls. Min: minute. WT: wild-type chimera.
FIG. 8C shows that mutation of all PTMs blocks the activation of ERK pathway. Activation of ERK pathway by the wild-type chimera and P1-6 was assessed by detecting phosphorylation of ERK using Western analysis with, antibodies against phospho-ERK (p-ERK). Immunoblots were stripped and then reprobed with antibodies against ERK as loading controls. Min: minute. WT: wild-type chimera.
FIG. 8D demonstrates that mutation of all PTMs blocks the activation of p38 pathway. Activation of p38 pathway by the wild-type chimera and P1-6 were assessed as phosphorylation of p38 using Western analysis with antibodies against phospho-p38 (p-p38). Immunoblots were stripped and then reprobed with antibodies against p38 as loading controls. Min: minute. WT: wild-type chimera.

First, TNFR1$^{-/-}$R2$^{-/-}$ BMMs were infected with virus encoding either the wild-type chimera or the mutant P1-6. Infected cells were then treated with TNFα for various times and the activation of the signaling pathways was determined by Western analysis (FIGS. 8A-8D). While the wild-type chimera induced the phosphorylation of IκB with 5 min treatment (lanes 1 and 2, FIG. 8A), P1-6 mutant failed to do so (lanes 5 and 6, FIG. 8A), indicating that some of the PTMs are implicated in activation of the IκB/NF-κB pathway. In addition, the wild-type chimera also led to a high level phosphorylation of JNK (lanes 1 and 2, FIG. 8B) and ERK (lanes 1 and 2, FIG. 8C) in response to TNFα treatment. In contrast, the TNFα-induced phosphorylation of JNK and ERK was profoundly reduced in the assays with P1-6 mutant (lanes 4 and 5, FIGS. 8B and 8C), revealing that one or more of PTMs mutated in P1-6 plays a role in activating the JNK and ERK pathway. Finally, a similar result was also obtained for p38 phosphorylation (FIG. 8D). Taken together, these data indicate that the PTMs 3, 5 or 6 may regulate osteoclast formation/function by activating NF-κB, JNK, ERK and/or p38 signaling pathways.

Figure 9:
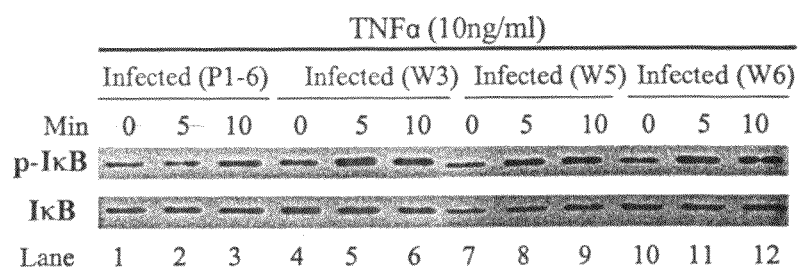
FIG. 9A describes activation of IκB/NF-κB pathway by W3, W5 and/or W6. BMMs infected with virus encoding P1-6, W3, W5 or W6 were treated with TNFα (10 ng/ml) for 0, 5 or 10 minutes (Min). Activation of IκB/NF-κB pathways was examined using Western analysis with antibodies against phospho-IκB (p-IκB) as described in FIGS. 8A-8D. Immunoblots were stripped and then reprobed with antibodies against IκB as loading controls.
FIG. 9B describes activation of JNK pathway by W3, W5 and/or W6. Activation of JNK pathways was examined using the same procedure as described in FIG. 9A except with antibodies against phospho-JNK (p-JNK). Antibodies against JNK were used as loading controls.
FIG. 9C describes activation of ERK pathway by W3, W5 and/or W6. Activation of ERK pathways was examined using the same procedure as described in FIG. 9A except with antibodies against phospho-ERK (p-ERK). Antibodies against ERK were used as loading controls.
FIG. 9D shows activation of p38 pathway by W3, W5 and/or W6. Activation of p38 pathways was examined using the same procedure as described in FIG. 9A except with antibodies against phospho-p38 (p-p38). Antibodies against p38 were used as loading controls.
Figure 9:
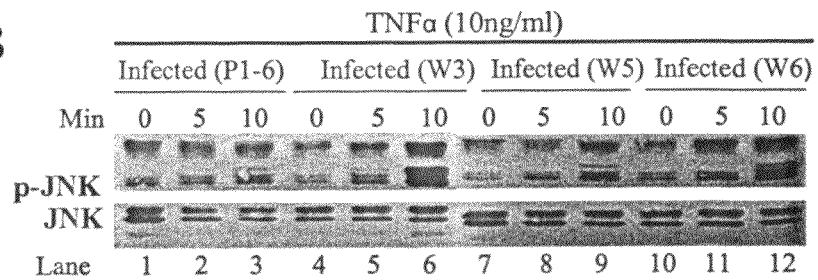
Figure 9:
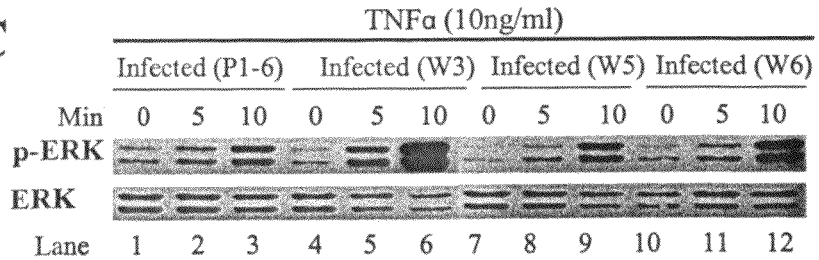
Figure 9:
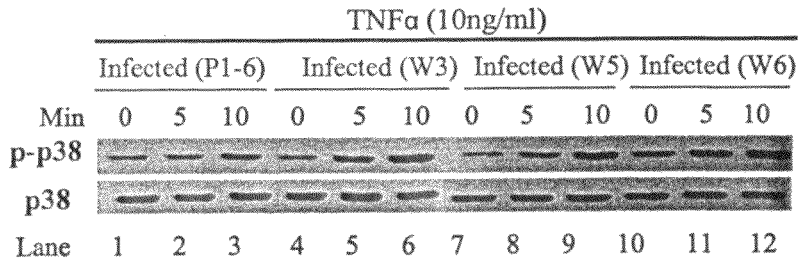
Figure 10:
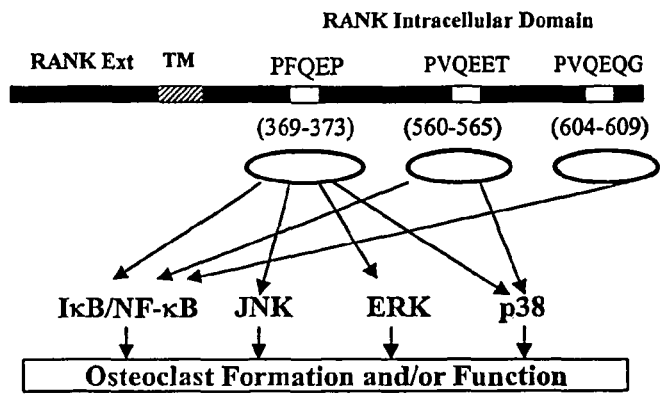
FIG. 10 is a summary of the signaling pathways activated by the three functional RANK cytoplasmic motifs (SEQ ID NOS 1-3, respectively, in order of appearance) (i.e., PTM3, PTM5, and PTM6). RANK Ext: RANK extracellular domain; TM: transmembrane domain.

Next, each of the three functional RANK motifs was examined to determine which motif can activate these signaling pathways in BMMs. Western analysis was repeated with P1-6, W3, W5 and W6 mutants, respectively (FIGS. 9A-9D). As shown in FIG. 9A, while P1-6 mutant failed to lead to IκB phosphorylation with 5 min treatment (lanes 1 and 2), W3, W5 and W6 all induced IκB phosphorylation (lanes 4 and 5, lanes 7 and 8, lanes 10 and 11), revealing that all three RANK motifs are able to activate IκB/NF-κB pathway. Moreover, W3 can significantly activate three MAPK pathways—namely, JNK (lanes 4, 5 and 6, FIG. 9B), ERK (lanes 4, 5 and 6, FIG. 9C); and p38 (lanes 4, 5 and 6, FIG. 9D) pathways. In addition, FIGS. 9A-9D show that W5 can induce p38 activation (lanes 7, 8, and 9, FIG. 9D). In summary, PFQEP$^{369\text{-}373}$ (PTM3, SEQ ID NO:1) is involved in the activation of IκB and three MAPK pathways; PVQEET$^{559\text{-}564}$ (PTM5, SEQ ID NO: 2) activates IκB and p38 pathways; and PVQEQG$^{604\text{-}609}$ (PTM6, SEQ ID NO: 3) is capable of activating IκB pathway (FIG. 10).

RANKL has been shown to play pivotal roles in regulating various biological processes such as bone homeostasis, immune function and mammary gland development. In addition, it has also been established that RANKL exerts its biological effects by binding to its receptor RANK, a member of the TNF receptor superfamily. However, the RANK-initiated intracellular signaling pathways in the various biological functions in response to RANKL ligation have not been fully defined.

Previous studies were mostly carried out either by in vitro binding assays or by using transformed cells irrelevant to osteoclasts, dendritic cells or mammary gland epithelial cells. See, e.g., Hsu, et al., Proc. Natl. Acad. Sci. U.S.A., 96:3540-3545 (1999); Darnay, et al. (1998, supra); Wong, et al. (supra); Kim, et al., (supra); Darnay, et al. (1999, supra); and Galibert, et al. (1998, supra). Therefore, the functional relevance of the data obtained from these studies to the three major biological processes has largely remained unknown. Moreover, it is controversial which TRAF proteins interact with RANK and which regions of the RANK interact with these TRAFs.

The above-described Examples focused on identification of structural determinants in RANK cytoplasmic domain that are involved in osteoclast formation and function. In order to obtain physiologically relevant data, structure-function study of RANK was carried out in primary osteoclast precursor cells, i.e., primary BMMs. This was successfully achieved by a combination of efficient transduction of genes into primary BMMs using retrovirus technology with the creation of a chimeric receptor approach (Feng, et al., ENDOCRINOL., 143: 4868-4874 (2002)) (FIG. 1B). Moreover, the other strength of these Examples is that a special emphasis was placed on identifying RANK cytoplasmic motifs that regulate cellular functions such as osteoclast formation and bone resorption. RANK contains either of three distinct motifs (PTM3, PTM5, and PTM6) were revealed to be capable of mediating osteoclast formation and function (FIG. 10).

PTM3 has been shown to be a TRAF6-binding motif (Ye, et al. (supra)). The above-described Examples revealed that RANK contains two more motifs (PTM5 and PTM6) that are able to promote osteoclast formation and function. PTM5 and PTM6 seem to be more potent in promoting osteoclast formation than PTM3 (FIGS. 6C and 6D). PTM5 and PTM6 motifs are located in the functional RANK regions revealed by Armstrong, et al. (supra).

Upon the identification of the functional RANK motifs, the above Examples further examined the capacity of these motifs to activate several known signaling pathways initiated by RANK. The data showed that while all three motifs are able to activate IκB/NF-κB pathway, they differ in their ability to activate MAPK pathways (FIGS. 9A-9D), indicating that these functional RANK motifs can play distinct roles in initiating intracellular signaling pathways. Research is underway to functionally identify TRAF proteins that specifically bind to these RANK motifs in transmitting intracellular signaling in osteoclast formation and function.

The above osteoclastogenesis assays also demonstrated that the RANK motifs exhibited distinct capacity in promoting osteoclast formation in the presence of M-CSF (FIGS. 6C and 6D). Both PTM5 and PTM6 appear to be more potent than PTM3 in forming osteoclasts. The signaling data further revealed that these motifs differ in their ability to mediate signaling pathways (FIGS. 9A-9D). In particular, they can activate different MAPK pathways. These data implicate that PTM5 and PTM6 may activate other yet unidentified pathways to promote osteoclast formation. Future studies aimed at addressing this issue may provide more insights into the signaling mechanism underling the RANKL-induced osteoclast formation.

Example 6

PTM3 Plays a Predominant Role in Osteoclast Survival by Activating AKT/PKB and its Downstream Effector AFX/FOXO4

RANKL has been known to play an important role in stimulating osteoclast survival. Consistent with the notion, OPG, the decoy receptor for RANKL, can inhibit osteoclast survival. RANKL has been postulated to exert its anti-apoptotic effects at least in part by activating Akt/protein kinase B (Akt/PKB) through a signaling complex involving TNF receptor associated factor 6 (TRAF6) and c-Src. In this model, RANKL induces TRAF6, c-Src, and RANK to form a trimer. Within this trimeric complex, TRAF6 induces the activation of c-Src which in turn activates phosphotidylinositol-3-kinase (PI3-kinase). The activated PI3-kinase then leads to the activation of Akt/PKB. Akt/PKB may utilize distinct downstream pathways (GSK3β, FKHR/FOXO1a, BAD or AFX/FOXO4) to regulate cell survival. However, the precise downstream signaling pathway activated by Akt/PKB to regulate osteoclast survival has still remained elusive.

As demonstrated in the above Examples, three RANK cytoplasmic motifs—namely, PTM3, PTM5, and PTM6—are involved in the regulation of osteoclast formation and function. These three motifs activate different signaling pathways. PTM3 activates NF-κB, JNK, ERK, and p38; PTM5 triggers the activation of NF-κB and p38; and PTM6 activates only NF-κB. However, the specific RANK cytoplasmic motifs and downstream signaling pathways involved in osteoclast survival have not been functionally identified.

In this Example, PTM3, PTM5, and PTM6 were evaluated for their involvements in modulating osteoclast survival. PTM3 was shown to be highly potent in promoting osteoclast survival in part by activating Akt/PBK pathway, although this motif seems to play a less prominent role in osteoclast formation and function. The downstream effector AFX/FOXO4 was also identified as being activated by Akt/PKB in osteoclast survival.

Figure 11:
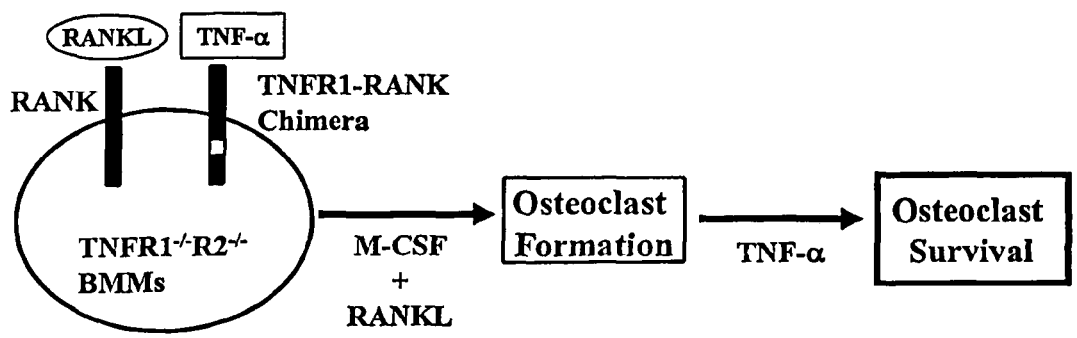
FIG. 11 shows the experimental strategy for identifying RANK motifs that modulate osteoclast survival. Mutant chimeric receptors as illustrated in FIG. 6A were used to determine their abilities to promote osteoclast survival.

The Chimeric Receptor Approach Permits the Investigation of RANK Signaling Involved in Osteoclast Survival The above Examples describe a chimeric receptor approach for delineating functional motifs in the RANK cytoplasmic domain mediating osteoclast differentiation and function. The chimeric receptor comprises mouse TNFR1 external domain linked to the transmembrane and intracellular domains of mouse RANK. In order to investigate the role of the six PTMs in osteoclast survival, mature osteoclasts expressing the six mutants W1-W6 were obtained. However, as illustrated above, while W3, W5 and W6 can promote osteoclast formation, W1, W2 and W4 are incapable of mediating osteoclast formation. However, the chimeric receptor approach possesses a unique "switch" feature that allows us to overcome the problem. As shown in FIG. 11, infected BMMs not only express a chimeric receptor but also retain endogenous RANK. As a result, infected BMMs can be treated with RANKL and M-CSF to stimulate osteoclast formation. Once osteoclasts are formed, M-CSF and RANKL are removed and the cultures are then treated with TNF-α alone to assess the impact of the expressed chimeric receptor on osteoclast survival (FIG. 11).

To determine whether the chimeric receptor approach indeed has the "switch" feature and whether RANK motifs mediating osteoclast survival are among the six PTMs, uninfected BMMs as well as infected BMMs expressing WT or P1-6 (FIG. 12A) were treated with M-CSF (22 ng/ml) and RANKL (100 ng/ml) to stimulate osteoclast formation (FIG. 12A). 4 days later, osteoclasts were formed, and a representative osteoclast culture is shown in FIG. 12A (top panel). Then, M-CSF and RANKL were removed and the cultures were treated with vehicle (PBS), M-CSF, RANKL, or TNF-α for 14 hours (FIG. 12A). Osteoclasts expressing wild-type chimera (WT) survived in response to M-CSF, RANKL, or TNF-α. As a negative control, osteoclasts derived from uninfected BMMs failed to survive in response to TNF-α. These data indicate that the chimeric receptor approach does possess the unique "switch" feature. In addition, while osteoclasts expressing WT survived with stimulation of TNF-α, those expressing P1-6 failed to do so, indicating that RANK motifs mediating osteoclast survival are indeed among the six PTMs. FIG. 12B shows the quantification of the data in FIG. 12A.

Identification of Three Functional RANK Motifs Mediating Osteoclast Survival

Figure 12:
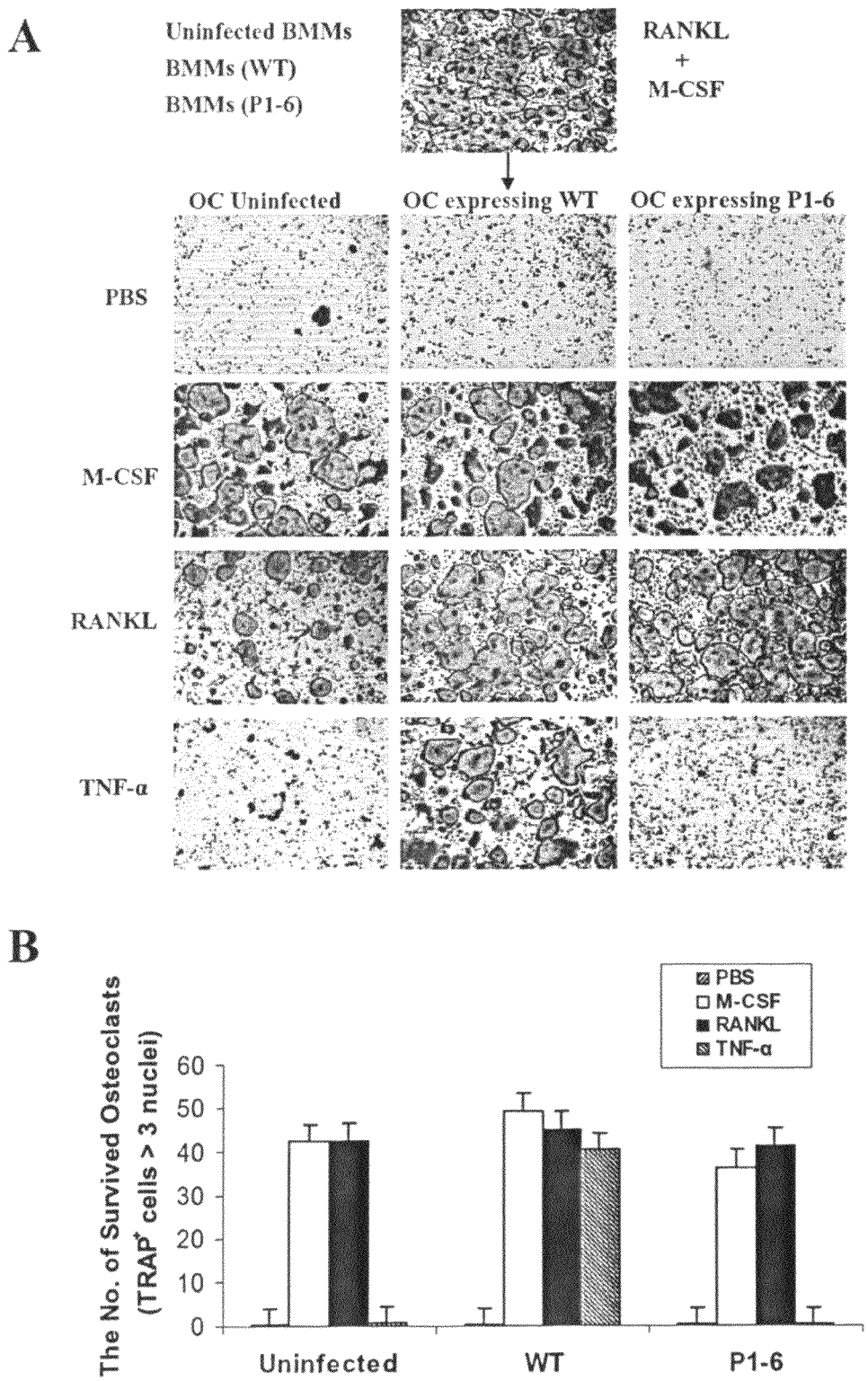
FIG. 12A demonstrates that the functional RANK motifs capable of mediating osteoclast survival are among the six PTMs. Osteoclast survival assays with WT and P1-6 are shown. Uninfected BMMs (TNFR1$^{-/-}$R2$^{-/-}$) and BMMs (TNFR1$^{-/-}$R2$^{-/-}$) infected with virus encoding WT or P1-6 were treated with RANKL (100 ng/ml) and M-CSF (22 ng/ml) for 4 days to promote osteoclast formation in 24-well plates. At day 4, the cultures were washed with PBS and then treated with vehicle (PBS), M-CSF (22 ng/ml), RANKL (100 ng/ml), or TNF-α (10 ng/ml). After 16 hours, the cultures were stained for TRAP activity. Each condition had three replicates (wells). A representative area of the cultures from each condition is shown. WT: wild type chimeric receptor, OC: osteoclasts.
FIG. 12B depicts the quantification of the osteoclast survival assays shown in FIG. 12A. Multinucleated TRAP positive cells (>3 nuclei) in three random view areas (at 100× magnification) were counted. The data indicate the averages of 3 counts±S.D.
Figure 13:
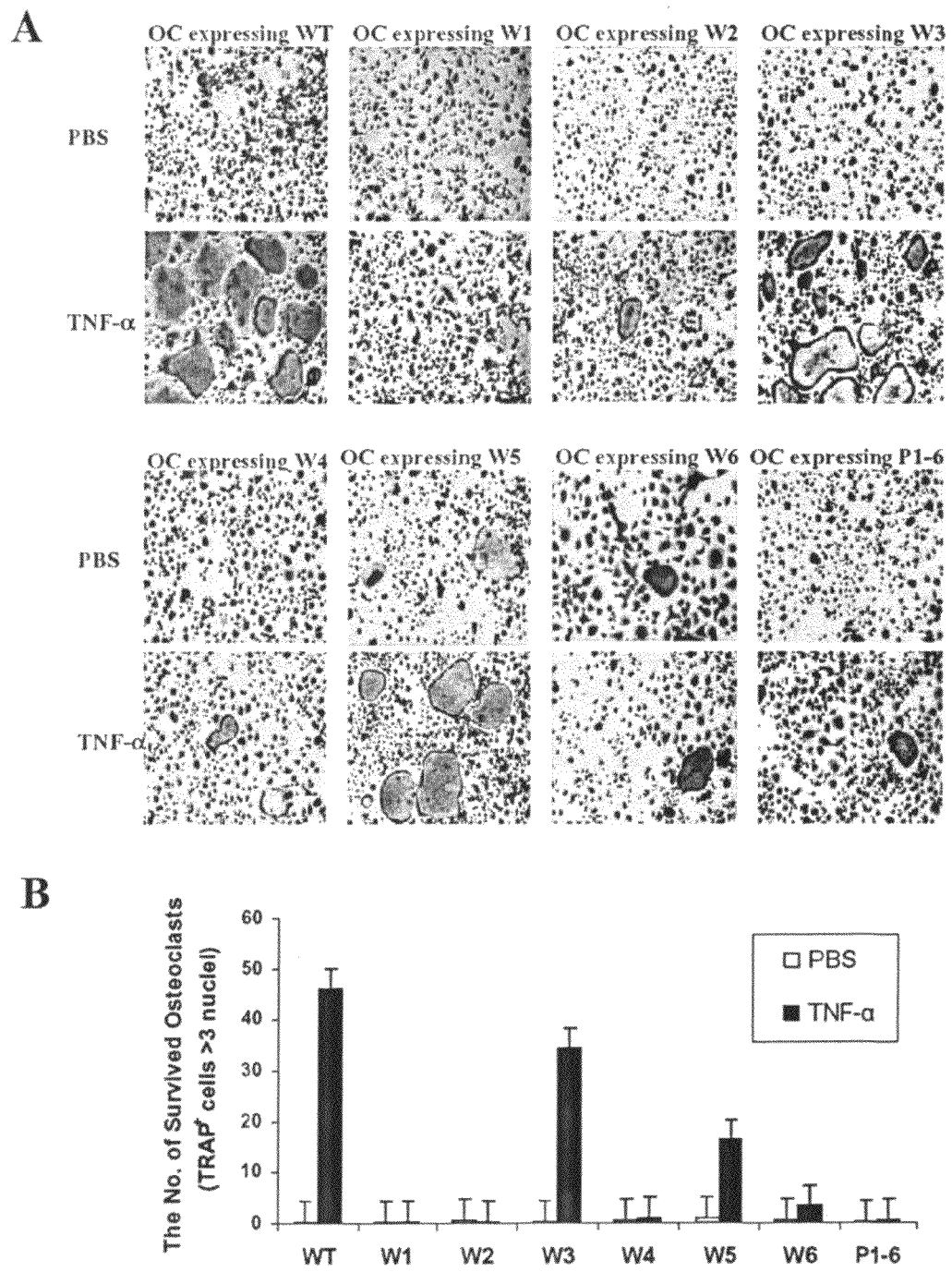
FIG. 13A shows that W3, W5 and W6 can promote osteoclast survival. Osteoclast assays were performed with WT, W1, W2, W3, W4, W5, W6 and P1-6 as described in FIG. 12A. Each condition had three replicates (wells). A representative area of the cultures from each condition is shown. WT: wild type chimeric receptor; OC: osteoclasts.
FIG. 13B is the quantification of the osteoclast survival assays shown in FIG. 13A. Multinucleated TRAP positive cells (>3 nuclei) in three random view areas (at 100× magnification) were counted. The data show the averages of 3 counts±S.D.

To identify the functional RANK cytoplasmic motifs, the osteoclast survival assay shown in FIG. 12 was repeated with mutant chimeras W1-W6 (FIG. 6A). WT was also used as a positive control and P1-6 as a negative control. In these assays, after the removal of M-CSF and RANKL, osteoclast cultures were treated with either PBS or TNF-α for 14 hours. As shown in FIG. 13A, while W1, W2 and W4 failed to promote osteoclast survival, W3, W5 and W6 were able to mediate osteoclast survival. The data shown in FIG. 13A are quantified in FIG. 13B. The survival assays also showed that the potency of these motifs in promoting osteoclast survival is in the order of W3>W5>W6. As shown in FIG. 6A, in W3 all PTMs except PTM3 are mutated. Similarly, in W5 and W6, all PTMs except PTM5 and PTM6, respectively, are mutated. Thus, PTM3, PTM5, and PTM6 appear to be the functional motifs capable of promoting osteoclast survival. PTM3, PTM5, and PTM6 are hereinafter referred to as Motif 1, Motif 2, and Motif 3, respectively.

Figure 14:
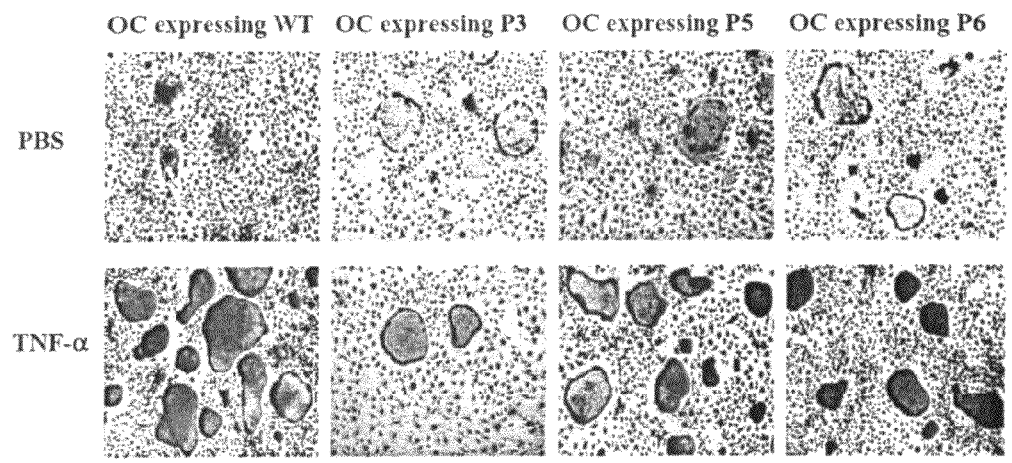
FIG. 14A demonstrates that P3, P5, and P6 have decreased capacity in modulating osteoclast survival. Osteoclast assays with WT, P3, P5, and P6 were performed as described in FIG. 12A. Each condition had three replicates (wells).A representative area of the cultures from each condition is shown. WT: wild type chimeric receptor; OC: osteoclasts.
FIG. 14B is the quantification of the osteoclast survival assays shown in FIG. 14A. Multinucleated TRAP positive cells (>3 nuclei) in three random view areas (at 100× magnification) were counted. The data show the averages of 3 counts±S.D.
Figure 14:
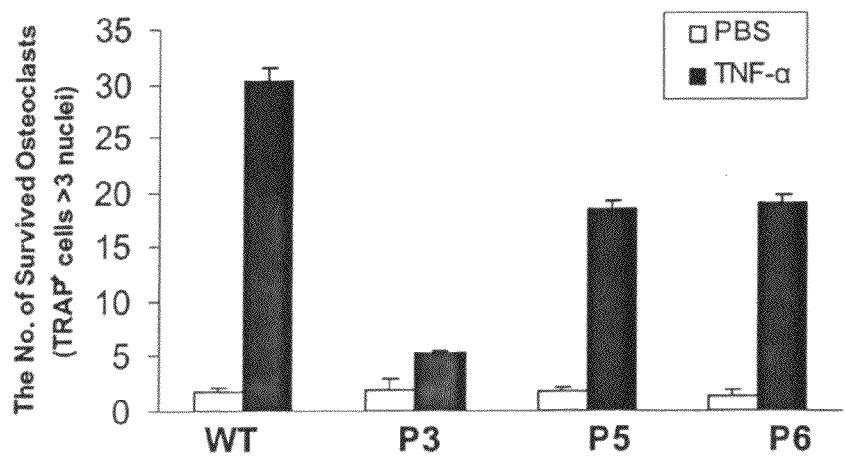

To further demonstrate that these three RANK motifs play functional role in osteoclast survival, the osteoclast survival assay was repeated with the mutant chimeric receptors P3, P5, and P6 (FIG. 3B). In P3, PTM3 (Motif 1) is mutated. In P5, PTM5 (Motif 2) is mutated. In P6, PTM6 (Motif 3) is mutated. FIG. 14A shows osteoclast cultures obtained from the survival assays, and the data are quantified in FIG. 14B. Consistent with the observation that PTM3 (Motif 1) played a predominant role in modulating osteoclast survival, P3 exhibited very low capacity in modulating osteoclast survival. In contrast, P5 and P6 had considerable ability to mediate osteoclast survival, indicating that PTM5 (Motif 2) and PTM6 (Motif 3) are less potent than PTM3 (Motif 1) in mediating osteoclast survival.

PTM3 (Motif 1), but not PTM5 (Motif 2) or PTM6 (Motif 3), Activates the Akt/PKB Pathway to Promote Osteoclast Survival RANK can activate at least six major pathways: NF-κB, JNK, ERK, p38, Akt/PKB, and NFATc1. Among them, NF-κB, ERK, and Akt/PKB are capable of modulating osteoclast survival. As shown above, PTM3 (Motif 1) can activate NF-κB and ERK, while PTM5 (Motif 2) and PTM6 (Motif 3) are able to activate NF-κB. To determine whether these three functional RANK motifs can also activate the Akt/PKB pathway, Western analysis was performed with an antibody against phosphorylated Akt/PKB.

Figure 15:
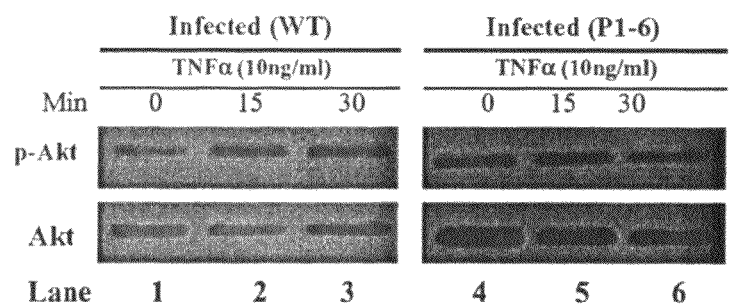
FIG. 15A demonstrates that PTM3 (Motif 1) is capable of activating the Akt/PKB pathway in BMMs. Activation of the Akt/PKB pathway in BMMs was assessed by detecting phosphorylation of Akt/PKB using Western analysis with an antibody against phospho-Akt (p-Akt). Immunoblots were, stripped and then reprobed with an antibody against Akt as loading controls. Min: minute.
FIG. 15B illustrates activation of the Akt/PKB pathway by W3, W5 and W6 in BMMs. The assays were performed as described in FIG. 15A.
Figure 15:
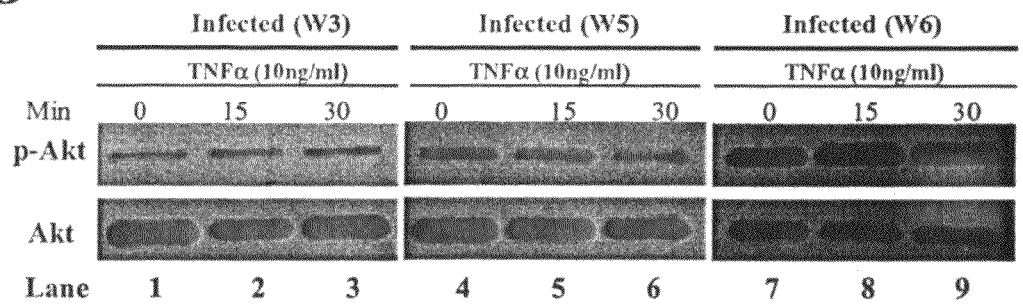

TNFR1$^{-/-}$R2$^{-/-}$ BMMs were first infected with virus encoding either the wild-type chimera or the mutant P1-6. Infected cells were then treated with TNF-α for various times and the activation of the Akt/PKB signaling pathway was monitored by Western analysis (FIG. 15A). While the wild-type chimera induced the phosphorylation of Akt/PKB with 15 and 30 min treatment (lanes 1, 2 and 3, FIG. 15A), P1-6 mutant failed to do so (lanes 4, 5 and 6, FIG. 15A), indicating that certain PTM(s) is involved in the activation of the Akt/PKB pathway. Western analysis was then repeated with W3, W5 and W6 mutants. As shown in FIG. 15B, W3 induced Akt/PKB phosphorylation with 15 and 30 min treatment (lanes 1, 2 and 3), while W5 and W6 failed to do so (lanes 4-9), suggesting that PTM3 (Motif 1) is primarily responsible for the activation of the Akt pathway.

Figure 16:
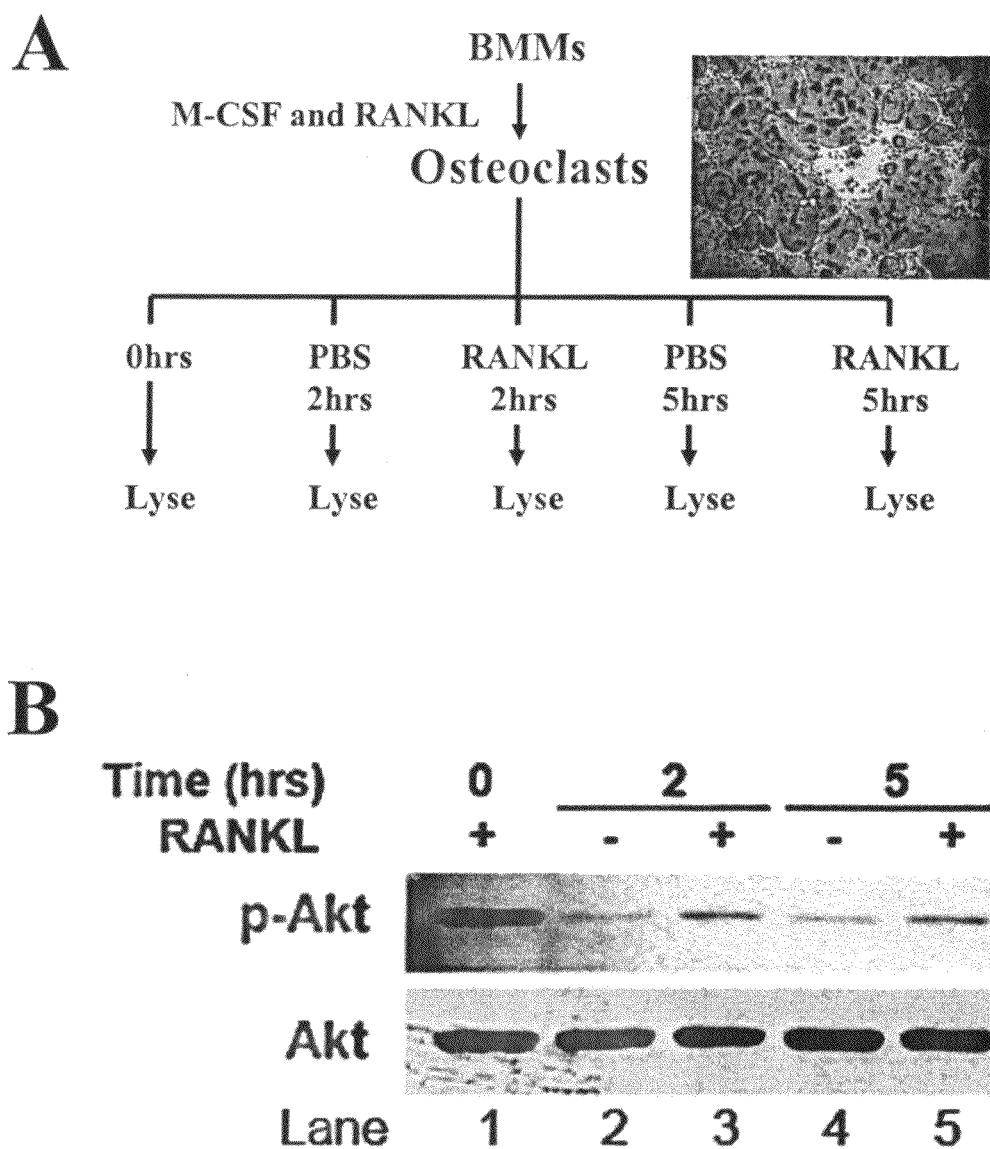
FIG. 16A schematically describes the experimental procedure for the detection of activation of the Akt pathway in mature osteoclasts. Hrs: hours.
FIG. 16B shows activation of the Akt/PKB pathway in osteoclasts. Phosphorylation of Akt/PKB was detected using Western analysis with an antibody against phospho-Akt (p-Akt). Immunoblots were stripped and then reprobed with an antibody against Akt/PKB as loading control. Min: minute.
Figure 17:
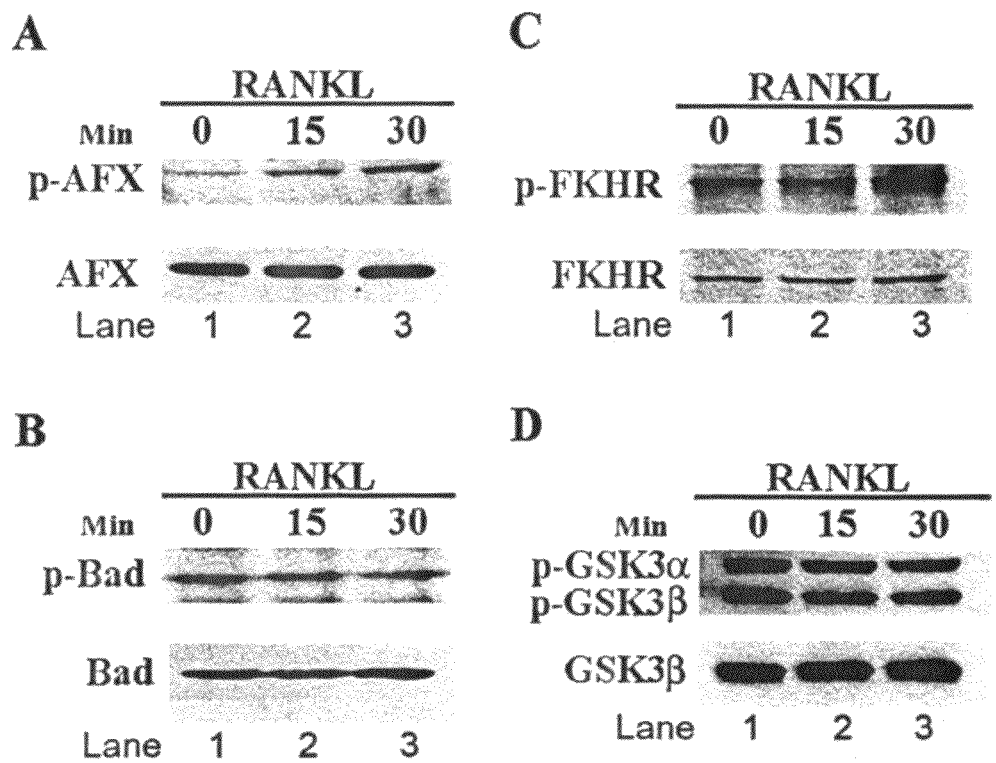
FIG. 17A depicts activation of the AFX/FOXO4 pathway by RANKL in BMMs. Activation of the AFX/FOXO4 pathway was assessed by detecting phosphorylation of the protein using Western analysis with an antibody against phospho-AFX (p-AFX). Immunoblots were stripped and then reprobed with an antibody against AFX as loading control.
FIG. 17B shows activation of the BAD pathway by RANKL in BMMs. Activation of the BAD pathway was assessed by detecting phosphorylation of the protein using Western analysis with an antibody against phospho-BAD (p-BAD). Immunoblots were stripped and then reprobed with an antibody against BAD as loading control.
FIG. 17C illustrates activation of the FKHR/FOXO1a pathway by RANKL in BMMs. Activation of the FKHR/FOXO1a pathway was assessed by detecting phosphorylation of the protein using Western analysis with an antibody against phospho-FKHR (p-FKHR). Immunoblots were stripped and then reprobed with an antibody against FKHR as loading control.
FIG. 17D depicts activation of the GSK3β pathway by RANKL in BMMs. Activation of the GSK3β pathway was assessed by detecting phosphorylation of the protein using Western analysis with an antibody against phospho-GSK3β (p-GSKα/β). Immunoblots were stripped and then reprobed with an antibody against GSK3β (3 as loading control.

Similar assays were repeated in mature osteoclasts to determine whether Akt/PKB can be activated by RANKL. Since most osteoclasts died after 16- or 8-hour starvation in α-MEM without serum, M-CSF or RANKL, a different experimental strategy as depicted in FIG. 16A was employed. First, BMMs were treated with M-CSF and RANKL to promote osteoclast formation. Once osteoclasts were formed, cells were either lysed immediately or lysed after having been treated with vehicle (PBS) or RANKL for 2 or 5 hours (FIG. 16A). The lysate were then used for Western analysis for the state of Akt/PKB activation (phosphorylation). As shown in FIG. 16B, Akt/PKB phosphorylation is decreased more dramatically in control cultures (lanes 2 and 4) than in the cells treated with RANKL (lanes 3 and 5), indicating that RANKL plays a role in activating Akt/PKB in mature osteoclasts.

AFX/FOXO4 is a Downstream Target of the Akt/PKB Pathway in Mediating Osteoclast Survival It has been established that Akt/PKB targets various downstream effectors such as GSK3β (glycogen synthase kinase 3 beta), BAD (BCL2-antagonist of cell death), FKHR/FOXO1a (forkhead box O1A (rhabdomyosarcoma)), and AFX/FOXO4 (ALL1 fused gene from chromosome X). To determine which downstream effector(s) the Akt/PKB pathway targets to promote osteoclast formation, Western analysis was performed with antibodies against phosphorylated forms of GSK3β, BAD, FKHR/FOXO1a and AFX/FOXO4. As shown in FIGS. 17A-D, RANKL treatment activated the phosphorylation of AFX/FOXO4 (lanes 2 and 3, FIG. 17A), but not BAD (FIG. 17B), FKHR/FOXO1a (FIG. 17C) and GSK3β (FIG. 17D) in BMMs.

Figure 18:
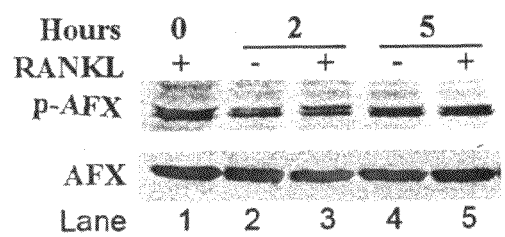
FIG. 18A illustrates activation of the AFX/FOXO4 pathway by RANKL in osteoclasts. Cell lysates were prepared as described in FIG. 16A. Western assays were performed as described in FIG. 17A.
FIG. 18B indicates activation of the BAD pathway by RANKL in osteoclasts. Cell lysates were prepared as described in FIG. 16A. Western assays were performed as described in FIG. 17B.
FIG. 18C demonstrates activation of the FKHR/FOXO1a pathway by RANKL in osteoclasts. Cell lysates were prepared as described in FIG. 16A. Western assays were performed as described in FIG. 17C.
FIG. 18D shows activation of the GSK3β pathway by RANKL in osteoclasts. Cell lysates were prepared as described in FIG. 16A. Western assays were performed as described in FIG. 17D.
Figure 18:
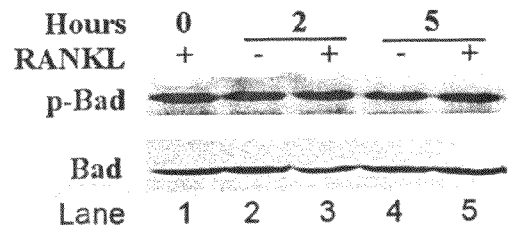
Figure 18:
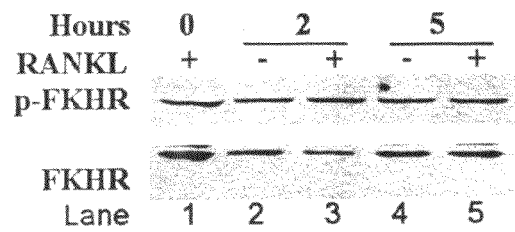
Figure 18:
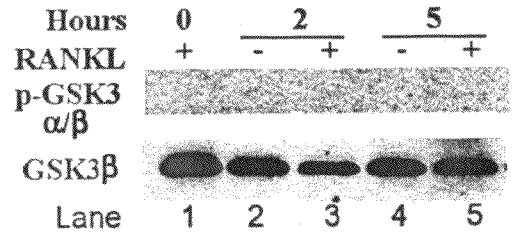

The activation of AFX/FOXO4 was also investigated in mature osteoclasts. BMMs were treated with M-CSF and RANKL to promote osteoclast formation as described in FIG. 16A. Once osteoclasts were formed, cells were either lysed immediately or lysed after having been treated with vehicle (PBS) or RANKL for 2 or 5 hours. The lysates were then used for Western analysis for the state of GSK3β, BAD, FKHR/FOXO1a and AFX/FOXO4 activation (phosphorylation). As shown in FIG. 18A, AFX/FOXO4 phosphorylation was decreased more dramatically in control cultures (lanes 2 and 4, the upper band represents the phosphorylated form of AFX/FOXO4) than in the cells treated with RANKL (lanes 3 and 5), indicating that RANKL plays a role in activating AFX/FOXO4 in mature osteoclasts. In contrast, RANKL failed to induce the activation of BAD (FIG. 18B), FKHR/FOXO1a (FIG. 18C), or GSK3β (FIG. 18D) in mature osteoclasts.

The control of osteoclast lifespan has been recognized as a critical regulatory factor in bone remodeling, and alteration in osteoclast lifespan is attributed to the pathogenesis of bone disorders including postmenopausal osteoporosis. Since the discovery of RANKL, RANKL has been shown to play important roles not only in osteoclast formation and function, but also in osteoclast survival. However, the molecular mechanism by which RANKL regulates osteoclast survival has not been fully understood.

RANKL exerts its functions by binding to and activating its receptor RANK, which recruits various TRAF proteins through specific motifs in the cytoplasmic domain upon activation. In the above Examples, three RANK cytoplasmic motifs (Motif 1, Motif 2, and Motif 3) were identified to be involved in the regulation of osteoclast formation and function. This Example further investigated the molecular mechanism by which RANKL regulates osteoclast survival, and identified RANK motifs that are responsible for osteoclast survival. It revealed that the same three motifs are involved in osteoclast survival. As noted above, Motif 1 is highly potent in mediating osteoclast survival although it plays a less prominent role in osteoclast differentiation and function (compare FIG. 6D with FIGS. 13A-B). In contrast, Motif 2 and Motif 3 are highly capable of mediating osteoclast formation and function, but are less effective in promoting osteoclast survival.

Akt/PKB is a potent factor regulating osteoclast survival in response to a variety of stimuli including RANKL, IL-1, and TNF-α. It has been reported that RANKL activates Akt/PKB through a signaling complex involving TRAF6 and c-Src (Wong et al., MOLECULAR CELL, 4:1041-1049 (1999)). To investigate the molecular mechanism by which the three RANK motifs modulate osteoclast survival, these motifs were examined to determine whether they are capable of activating Akt/PKB. The data indicated that Motif 1, but not Motif 2 or Motif 3, is able to activate Akt/PKB. The above Examples demonstrate that Motif 2 and Motif 3 can activate NF-κB pathway, while Motif 1 can activate both NF-κB and ERK pathways. Because both NF-κB and ERK are mediators of osteoclast survival, these data explain why Motif 1 appears to be more potent than Motif 2 and Motif 3 in promoting osteoclast survival. This theory is summarized in FIG. 19.

It has been established that Akt/PKB may utilize distinct downstream effectors such as p21CIP1, MDM2, TSC2, eNOS, GSK3β, FKHR/FOXO1a, BAD and AFX/FOXO4 to regulate a variety of cellular processes such as cell proliferation, growth and survival. Among these diverse effectors, GSK3β (3, FKHR/FOXO1a, BAD and AFX/FOXO4 are believed to play roles in cell survival. This study further determined that AFX/FOXO4 is the downstream effector activated by Akt/PKB in promoting osteoclast survival.

AFX (ALL1 fused gene from chromosome X), also known as FOXO4, is a transcription factor belonging to the Forkhead transcription factor superfamily. AFX was identified as a mammalian homolog of the Forkhead transcription factor daf-16 in *Caenorhabditis elegans*. The Forkhead superfamily contains more than 100 members identified in different species and about 0.40 mammalian homologs have been identified. Members of this superfamily are characterized by the presence of a highly conserved DNA-binding domain known as the Forkhead box, which was named based on its homology to the DNA-binding domain of the Drosophila homeotic Forkhead protein and the hepatic nuclear factor-3 (HNF-3) transcription factors. Given that members of the Forkhead superfamily are highly divergent outside of the Forkhead box, Forkhead transcription factors have been further categorized into 17 subfamilies ranging from FOXA to FOXQ.

Figure 19:
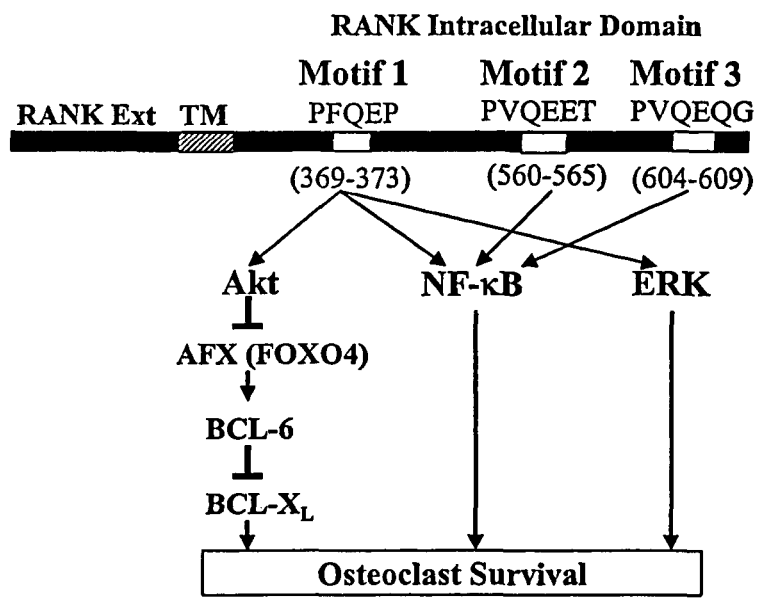
FIG. 19 is a diagram showing the RANKL-mediated signaling pathways involved in osteoclast survival.

AFX belongs to the FOXO subfamily which comprises several other members including FOXO1a (FKHR) and FOXO3a (FKHRL1). The FOXO factors have been shown to play important roles in cell proliferation and survival. Activation of a FOXO factor is sufficient to induce the expression of proapoptotic genes and trigger apoptosis in cells of hematopoietic origin. Phosphorylation of a FOXO factor by Akt/PKB also causes its retention in cytoplasm and/or its translocation from the nucleus to cytoplasm, resulting in the inhibition of the transcriptional activation of the proapoptotic genes. Although FOXO1a (FKHR) and FOXO4 (AFX) are downstream targets of Akt/PKB, only AFX/FOXO4 appears to be involved in RANKL-mediated osteoclast survival. It is speculated that AFX/FOXO4 can activate apoptosis by inducing the expression of the BCL-6 transcriptional repressor (FIG. 19; Tang et al., J. BIOL. CHEM., 277:14255-14265 (2002)). The BCL-6 promoter contains multiple binding sites for AFX/FOXO4. BCL-6 then regulates apoptosis by regulating the expression of BCL-XL, an anti-apoptotic protein (FIG. 19). It has also been noted that macrophages isolated from BCL-6$^{-/-}$ exhibited enhanced survival, supporting the potential role of BCL-6 in AFX-induced osteoclast precursor survival. In line with this theory, this Example indicates that AFX/FOXO4 is phosphorylated in response to RANKL stimulation.

It is also noted that the AFX/FOXO4$^{-/-}$ mice are viable and no apparent abnormalities have been identified. However, it is not clear whether the skeletal development and, especially, osteoclast survival in these mice have been carefully examined. Given that AFX/FOXO4 pathway may represent only one of numerous pathways implicated in regulating osteoclast survival (FIG. 19), AFX/FOXO4$^{-/-}$ osteoclasts are likely to exhibit only subtle difference in osteoclast survival as compared to wild-type controls. As a result, any potential in vivo phenotypes might only be detectable in older mice. Thus, a careful examination of the AFX/FOXO4$^{-/-}$ mice is needed to determine whether any abnormality in osteoclast survival results from the deletion of the gene for AFX/FOXO4.

The foregoing description of the invention provides illustration and description, but is not intended to be exhaustive or to limit the invention to the precise one disclosed. Modifications and variations are possible consistent with the above teachings or may be acquired from practice of the invention. Thus, it is noted that the scope of the invention is defined by the claims and their equivalents.

What is claimed is:

1. An isolated molecule of interest that modulates a RANK-mediated signaling pathway through one or more TNF receptor associated factors (TRAF) binding motif ("PTM motif"), wherein said isolated molecule of interest comprises a PTM3 motif having an amino acid sequence PFSEP (SEQ ID NO:4) or PFQEP (SEQ ID NO: 1), a PTM5 motif having an amino acid sequence PVQEET (SEQ ID NO:2), and a PTM6 motif having an amino acid sequence PVQEQG (SEQ ID NO:3).

2. The isolated molecule of interest of claim 1, wherein said isolated molecule of interest comprises a PTM3 motif having an amino acid sequence PFSEP (SEQ ID NO:4), a PTM5 motif having an amino acid sequence PVQEET (SEQ ID NO:2), and a PTM6 motif having an amino acid sequence PVQEQG (SEQ ID NO:3).

3. The isolated molecule of interest of claim 1, wherein said isolated molecule of interest comprises a PTM3 motif having an amino acid sequence PFQEP (SEQ ID NO: 1), a PTM5 motif having an amino acid sequence PVQEET (SEQ ID NO:2), and a PTM6 motif having an amino acid sequence PVQEQG (SEQ ID NO:3).

4. A composition comprising a molecule of interest of claim 1, wherein said composition is capable of modulating a PTM3-mediated RANK signaling pathway.

5. composition comprising a molecule of interest of claim 1, wherein said composition is capable of modulating a PTM5-mediated RANK signaling pathway.

6. A composition comprising a molecule of interest of claim 1, wherein said composition is capable of modulating a PTM6-mediated RANK signaling pathway.

7. A composition comprising one or more molecule of claim 1, wherein said molecule modulates at least two RANK-mediated pathways selected from a PTM3-mediated RANK signaling pathway, a PTM5-mediated RANK signaling pathway, and a PTM6-mediated RANK signaling pathway.

8. An isolated chimeric transmembrane protein comprising an extracellular domain of a non-RANK TNFR superfamily member selected from the group consisting of TNFR1, TNFR2, Fas, and CD40 and a RANK intracellular domain comprising one or more PTM motifs, wherein said PTM motif is PTM3 motif having an amino acid sequence PFSEP (SEQ ID NO:4) or PFQEP (SEQ ID NO:1), PTM5 motif having an amino acid sequence PVQEET (SEQ ID NO:2), or PTM6 motif having an amino acid sequence PVQEQG (SEQ ID NO:3).

9. The chimeric transmembrane protein of claim 8, wherein said RANK intracellular domain comprises PTM3 motif having an amino acid sequence PFSEP (SEQ ID NO:4) or PFQEP (SEQ ID NO:1).

10. The chimeric transmembrane protein of claim 8, wherein said RANK intracellular domain comprises PTM5 motif having an amino acid sequence PVQEET (SEQ ID NO:2).

11. The chimeric transmembrane protein of claim 8, wherein said RANK intracellular domain comprises PTM6 motif having an amino acid sequence PVQEQG (SEQ ID NO:3).

12. The chimeric transmembrane protein of claim 9, wherein said RANK intracellular domain comprises PTM3 motif having an amino acid sequence PFSEP (SEQ ID NO:4) or PFQEP (SEQ ID NO: 1) but not PTM5 or PTM6 motif, or both.

13. The chimeric transmembrane protein of claim 10, wherein said RANK intracellular domain comprises PTM5 motif having an amino acid sequence PVQEET (SEQ ID NO:2) but not PTM3 or PTM6 motif, or both.

14. The chimeric transmembrane protein of claim 11, wherein said RANK intracellular domain comprises PTM6 motif having an amino acid sequence PVQEQG (SEQ ID NO:3) but not PTM3 or PTM5 motif, or both.

* * * * *

SEQUENCE LISTING

<160> NUMBER OF SEQ ID NOS: 41

<210> SEQ ID NO 1
<211> LENGTH: 5
<212> TYPE: PRT
<213> ORGANISM: Mus musculus

```
<400> SEQUENCE: 1

Pro Phe Gln Glu Pro
1               5

<210> SEQ ID NO 2
<211> LENGTH: 6
<212> TYPE: PRT
<213> ORGANISM: Mus musculus

<400> SEQUENCE: 2

Pro Val Gln Glu Glu Thr
1               5

<210> SEQ ID NO 3
<211> LENGTH: 6
<212> TYPE: PRT
<213> ORGANISM: Mus musculus

<400> SEQUENCE: 3

Pro Val Gln Glu Gln Gly
1               5

<210> SEQ ID NO 4
<211> LENGTH: 5
<212> TYPE: PRT
<213> ORGANISM: Homo sapiens

<400> SEQUENCE: 4

Pro Phe Ser Glu Pro
1               5

<210> SEQ ID NO 5
<211> LENGTH: 31
<212> TYPE: PRT
<213> ORGANISM: Mus musculus

<400> SEQUENCE: 5

Gly Ser Lys Ser Ile Pro Pro Phe Gln Glu Pro Leu Glu Val Gly Glu
1               5                   10                  15

Asn Asp Ser Leu Ser Gln Cys Phe Thr Gly Thr Glu Ser Thr Val
            20                  25                  30

<210> SEQ ID NO 6
<211> LENGTH: 24
<212> TYPE: PRT
<213> ORGANISM: Mus musculus

<400> SEQUENCE: 6

Glu Pro Glu Ser Glu Pro Val Gly Arg Pro Val Gln Glu Glu Thr Leu
1               5                   10                  15

Ala His Arg Asp Ser Phe Ala Gly
            20

<210> SEQ ID NO 7
<211> LENGTH: 13
<212> TYPE: PRT
<213> ORGANISM: Mus musculus

<400> SEQUENCE: 7

Thr Ser Arg Pro Val Gln Glu Gln Gly Gly Ala Gln Thr
1               5                   10

<210> SEQ ID NO 8
```

```
<211> LENGTH: 31
<212> TYPE: PRT
<213> ORGANISM: Homo sapiens

<400> SEQUENCE: 8

Gly Ser Lys Ser Thr Pro Pro Phe Ser Glu Pro Leu Glu Val Gly Glu
1               5                   10                  15

Asn Asp Ser Leu Ser Gln Cys Phe Thr Gly Thr Gln Ser Thr Val
            20                  25                  30

<210> SEQ ID NO 9
<211> LENGTH: 21
<212> TYPE: PRT
<213> ORGANISM: Homo sapiens

<400> SEQUENCE: 9

Ala Glu Pro Met Gly Arg Pro Val Gln Glu Glu Thr Leu Ala Arg Arg
1               5                   10                  15

Asp Ser Phe Ala Gly
            20

<210> SEQ ID NO 10
<211> LENGTH: 12
<212> TYPE: PRT
<213> ORGANISM: Homo sapiens

<400> SEQUENCE: 10

Ala Ser Arg Pro Val Gln Glu Gln Gly Gly Ala Lys
1               5                   10

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgtgtgaag gtgtcgtagt attgtctctg gacgacaaga tggttcc              47

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaaccatct tgtcgtccag agacaatacg acaccttcac acac                 44

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagtacacgg accggctcac gaagcttacg actggttcac tg                   42

<210> SEQ ID NO 14
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagtgaacca gtcgtaaggt tcgtgagccg gtccgtgtac tc                              42

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcaaatctat accccatgg aacgacctcc tggaagtggg g                                41

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccccacttcc aggaggtcgt tccatagggg tatagatttg c                               41

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacatcatcg tggtgtttct caccaactcc acgaacgacg gcccgggttc                      50

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggaacccggg ccgtcgttcg tggagttggt gagaaacagc acgatgatgt c                    51

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cccgtgggcc gccttctgaa cgacgactcg ctggcacac                                  39

<210> SEQ ID NO 20
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 20
gtgtgccagc gagtcgtcgt tcagaaggcg gcccacggg                              39

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggacatcgc ggctgctgaa cgacaacgct ggggcgcag                              39

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgcgcccca gttgtcgttc agcagccgcg atgtccc                                37

<210> SEQ ID NO 23
<211> LENGTH: 8
<212> TYPE: PRT
<213> ORGANISM: Mus musculus

<400> SEQUENCE: 23

Ile Leu Leu Met Thr Arg Glu Glu
1               5

<210> SEQ ID NO 24
<211> LENGTH: 5
<212> TYPE: PRT
<213> ORGANISM: Mus musculus

<400> SEQUENCE: 24

Pro Ser Gln Pro Ser
1               5

<210> SEQ ID NO 25
<211> LENGTH: 9
<212> TYPE: PRT
<213> ORGANISM: Mus musculus

<400> SEQUENCE: 25

Val Tyr Val Ser Gln Thr Ser Gln Glu
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated version of putative TRAF-binding motifs
      (PTM)-1
```

```
<400> SEQUENCE: 26

Val Val Val Leu Ser Leu Asp Asp
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated version of putative TRAF-Binding Motifs
      (PTM)-2

<400> SEQUENCE: 27

Leu Thr Asn Leu Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated version of putative TRAF-Binding Motifs
      (PTM)-3

<400> SEQUENCE: 28

Leu Trp Asn Asp Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated version of Putative TRAF-Binding Motifs
      (PTM)-4

<400> SEQUENCE: 29

Leu Phe Leu Thr Asn Ser Thr Asn Asp
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated version of Putative TRAF-Binding Motifs
      (PTM)-5

<400> SEQUENCE: 30

Leu Leu Asn Asp Asp Ser
1               5

<210> SEQ ID NO 31
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<223> OTHER INFORMATION: Mutated version of Putative TRAF-Binding Motifs
      (PTM)-6

<400> SEQUENCE: 31

Leu Leu Asn Asp Asn Ala
1               5

<210> SEQ ID NO 32
<211> LENGTH: 625
<212> TYPE: PRT
<213> ORGANISM: Mus musculus

<400> SEQUENCE: 32

Met Ala Pro Arg Ala Arg Arg Arg Gln Leu Pro Ala Pro Leu Leu
1               5                   10                  15

Ala Leu Cys Val Leu Leu Val Pro Leu Gln Val Thr Leu Gln Val Thr
                20                  25                  30

Pro Pro Cys Thr Gln Glu Arg His Tyr Glu His Leu Gly Arg Cys Cys
            35                  40                  45

Ser Arg Cys Glu Pro Gly Lys Tyr Leu Ser Ser Lys Cys Thr Pro Thr
    50                  55                  60

Ser Asp Ser Val Cys Leu Pro Cys Gly Pro Asp Glu Tyr Leu Asp Thr
65                  70                  75                  80

Trp Asn Glu Glu Asp Lys Cys Leu Leu His Lys Val Cys Asp Ala Gly
                85                  90                  95

Lys Ala Leu Val Ala Val Asp Pro Gly Asn His Thr Ala Pro Arg Arg
                100                 105                 110

Cys Ala Cys Thr Ala Gly Tyr His Trp Asn Ser Asp Cys Glu Cys Cys
            115                 120                 125

Arg Arg Asn Thr Glu Cys Ala Pro Gly Phe Gly Ala Gln His Pro Leu
    130                 135                 140

Gln Leu Asn Lys Asp Thr Val Cys Thr Pro Cys Leu Leu Gly Phe Phe
145                 150                 155                 160

Ser Asp Val Phe Ser Ser Thr Asp Lys Cys Lys Pro Trp Thr Asn Cys
                165                 170                 175

Thr Leu Leu Gly Lys Leu Glu Ala His Gln Gly Thr Thr Glu Ser Asp
                180                 185                 190

Val Val Cys Ser Ser Ser Met Thr Leu Arg Arg Pro Lys Glu Ala
            195                 200                 205

Gln Ala Tyr Leu Pro Ser Leu Ile Val Leu Leu Phe Ile Ser Val
    210                 215                 220

Val Val Val Ala Ala Ile Ile Phe Gly Val Tyr Tyr Arg Lys Gly Gly
225                 230                 235                 240

Lys Ala Leu Thr Ala Asn Leu Trp Asn Trp Val Asn Asp Ala Cys Ser
                245                 250                 255

Ser Leu Ser Gly Asn Lys Glu Ser Ser Gly Asp Arg Cys Ala Gly Ser
                260                 265                 270

His Ser Ala Thr Ser Ser Gln Gln Glu Val Cys Glu Gly Ile Leu Leu
            275                 280                 285

Met Thr Arg Glu Glu Lys Met Val Pro Glu Asp Gly Ala Gly Val Cys
    290                 295                 300

Gly Pro Val Cys Ala Ala Gly Gly Pro Trp Ala Glu Val Arg Asp Ser
305                 310                 315                 320
```

```
Arg Thr Phe Thr Leu Val Ser Glu Val Glu Thr Gln Gly Asp Leu Ser
            325                 330                 335
Arg Lys Ile Pro Thr Glu Asp Glu Tyr Thr Asp Arg Pro Ser Gln Pro
            340                 345                 350
Ser Thr Gly Ser Leu Leu Leu Ile Gln Gln Gly Ser Lys Ser Ile Pro
            355                 360                 365
Pro Phe Gln Glu Pro Leu Glu Val Gly Glu Asn Asp Ser Leu Ser Gln
            370                 375                 380
Cys Phe Thr Gly Thr Glu Ser Thr Val Asp Ser Glu Gly Cys Asp Phe
385                 390                 395                 400
Thr Glu Pro Pro Ser Arg Thr Asp Ser Met Pro Val Ser Pro Glu Lys
            405                 410                 415
His Leu Thr Lys Glu Ile Glu Gly Asp Ser Cys Leu Pro Trp Val Val
            420                 425                 430
Ser Ser Asn Ser Thr Asp Gly Tyr Thr Gly Ser Gly Asn Thr Pro Gly
            435                 440                 445
Glu Asp His Glu Pro Phe Pro Gly Ser Leu Lys Cys Gly Pro Leu Pro
            450                 455                 460
Gln Cys Ala Tyr Ser Met Gly Phe Pro Ser Glu Ala Ala Ala Ser Met
465                 470                 475                 480
Ala Glu Ala Gly Val Arg Pro Gln Asp Arg Ala Asp Glu Lys Gly Ala
            485                 490                 495
Ser Gly Ser Gly Ser Ser Pro Ser Asp Gln Pro Pro Ala Ser Gly Asn
            500                 505                 510
Val Thr Gly Asn Ser Asn Ser Thr Phe Ile Ser Ser Gly Gln Val Met
            515                 520                 525
Asn Phe Lys Gly Asp Ile Ile Val Val Tyr Val Ser Gln Thr Ser Gln
            530                 535                 540
Glu Gly Pro Gly Ser Ala Glu Pro Glu Ser Glu Pro Val Gly Arg Pro
545                 550                 555                 560
Val Gln Glu Glu Thr Leu Ala His Arg Asp Ser Phe Ala Gly Thr Ala
            565                 570                 575
Pro Arg Phe Pro Asp Val Cys Ala Thr Gly Ala Gly Leu Gln Glu Gln
            580                 585                 590
Gly Ala Pro Arg Gln Lys Asp Gly Thr Ser Arg Pro Val Gln Glu Gln
            595                 600                 605
Gly Gly Ala Gln Thr Ser Leu His Thr Gln Gly Ser Gly Gln Cys Ala
            610                 615                 620
Glu
625

<210> SEQ ID NO 33
<211> LENGTH: 616
<212> TYPE: PRT
<213> ORGANISM: Homo sapiens

<400> SEQUENCE: 33

Met Ala Pro Arg Ala Arg Arg Arg Pro Leu Phe Ala Leu Leu Leu Leu
1               5                   10                  15
Leu Cys Ala Leu Leu Ala Arg Leu Gln Val Ala Leu Gln Ile Ala Pro
            20                  25                  30
Pro Cys Thr Ser Glu Lys His Tyr Glu His Leu Gly Arg Cys Cys Asn
            35                  40                  45
Lys Cys Glu Pro Gly Lys Tyr Met Ser Ser Lys Cys Thr Thr Thr Ser
```

```
            50                  55                  60

Asp Ser Val Cys Leu Pro Cys Gly Pro Asp Glu Tyr Leu Asp Ser Trp
 65                  70                  75                  80

Asn Glu Glu Asp Lys Cys Leu Leu His Lys Val Cys Asp Thr Gly Lys
                 85                  90                  95

Ala Leu Val Ala Val Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
            115                 120                 125

Arg Asn Thr Glu Cys Ala Pro Gly Leu Gly Ala Gln His Pro Leu Gln
130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
            165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
            195                 200                 205

Val Tyr Leu Pro Gly Leu Ile Ile Leu Leu Leu Phe Ala Ser Val Ala
            210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
            245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
            275                 280                 285

Thr Leu Glu Glu Lys Thr Phe Pro Glu Asp Met Cys Tyr Pro Asp Gln
            290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
            325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
            355                 360                 365

Lys Ser Thr Pro Pro Phe Ser Glu Pro Leu Glu Val Gly Glu Asn Asp
            370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
            405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
            435                 440                 445

Cys Arg Asn Pro Pro Gly Glu Asp Cys Glu Pro Leu Val Gly Ser Pro
450                 455                 460

Lys Arg Gly Pro Leu Pro Gln Cys Ala Tyr Gly Met Gly Leu Pro Pro
465                 470                 475                 480
```

-continued

```
Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
        515                 520                 525

Ser Asn Ser Thr Phe Ile Ser Ser Gly Gln Val Met Asn Phe Lys Gly
    530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
        595                 600                 605

Gln Glu Gln Gly Gly Ala Lys Ala
    610                 615

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      consensus oligonucleotide

<400> SEQUENCE: 34 gggamttycc                                                              10

<210> SEQ ID NO 35
<211> LENGTH: 10
<212> TYPE: DNA
<213> ORGANISM: Homo sapiens

<400> SEQUENCE: 35
gggactttcc                                                              10

<210> SEQ ID NO 36
<211> LENGTH: 10
<212> TYPE: DNA
<213> ORGANISM: Homo sapiens

<400> SEQUENCE: 36
gggaatttcc                                                              10

<210> SEQ ID NO 37
<211> LENGTH: 17
<212> TYPE: DNA
<213> ORGANISM: Mus musculus

<400> SEQUENCE: 37
actggggaaa ttagggg                                                      17

<210> SEQ ID NO 38
<211> LENGTH: 13
<212> TYPE: DNA
<213> ORGANISM: Artificial Sequence
<220> FEATURE:
<223> OTHER INFORMATION: Description of Artificial Sequence: Synthetic
      consensus oligonucleotide
```

-continued

```
<220> FEATURE:
<221> NAME/KEY: modified_base
<222> LOCATION: (3)..(3)
<223> OTHER INFORMATION: a, c, t, g, unknown or other

<400> SEQUENCE: 38
smnrtmaaya kks                                                          13

<210> SEQ ID NO 39
<211> LENGTH: 13
<212> TYPE: DNA
<213> ORGANISM: Homo sapiens

<400> SEQUENCE: 39
ccagcaaaca gca                                                          13

<210> SEQ ID NO 40
<211> LENGTH: 13
<212> TYPE: DNA
<213> ORGANISM: Homo sapiens

<400> SEQUENCE: 40
gacacaaaca ggt                                                          13

<210> SEQ ID NO 41
<211> LENGTH: 454
<212> TYPE: PRT
<213> ORGANISM: Mus musculus

<400> SEQUENCE: 41
```

Met Gly Leu Pro Thr Val Pro Gly Leu Leu Leu Ser Leu Val Leu Leu
1               5                   10                  15

Ala Leu Leu Met Gly Ile His Pro Ser Gly Val Thr Gly Leu Val Pro
            20                  25                  30

Ser Leu Gly Asp Arg Glu Lys Arg Asp Ser Leu Cys Pro Gln Gly Lys
        35                  40                  45

Tyr Val His Ser Lys Asn Asn Ser Ile Cys Cys Thr Lys Cys His Lys
    50                  55                  60

Gly Thr Tyr Leu Val Ser Asp Cys Pro Ser Pro Gly Arg Asp Thr Val
65                  70                  75                  80

Cys Arg Glu Cys Glu Lys Gly Thr Phe Thr Ala Ser Gln Asn Tyr Leu
                85                  90                  95

Arg Gln Cys Leu Ser Cys Lys Thr Cys Arg Lys Glu Met Ser Gln Val
            100                 105                 110

Glu Ile Ser Pro Cys Gln Ala Asp Lys Asp Thr Val Cys Gly Cys Lys
        115                 120                 125

Glu Asn Gln Phe Gln Arg Tyr Leu Ser Glu Thr His Phe Gln Cys Val
    130                 135                 140

Asp Cys Ser Pro Cys Phe Asn Gly Thr Val Thr Ile Pro Cys Lys Glu
145                 150                 155                 160

Thr Gln Asn Thr Val Cys Asn Cys His Ala Gly Phe Phe Leu Arg Glu
                165                 170                 175

Ser Glu Cys Val Pro Cys Ser His Cys Lys Lys Asn Glu Glu Cys Met
            180                 185                 190

Lys Leu Cys Leu Pro Pro Leu Ala Asn Val Thr Asn Pro Gln Asp
        195                 200                 205

Ser Gly Thr Ala Val Leu Leu Pro Leu Val Ile Leu Leu Gly Leu Cys
    210                 215                 220

```
Leu Leu Ser Phe Ile Phe Ile Ser Leu Met Cys Arg Tyr Pro Arg Trp
225             230                 235                 240

Arg Pro Glu Val Tyr Ser Ile Ile Cys Arg Asp Pro Val Pro Val Lys
            245                 250                 255

Glu Glu Lys Ala Gly Lys Pro Leu Thr Pro Ala Pro Ser Pro Ala Phe
            260                 265                 270

Ser Pro Thr Ser Gly Phe Asn Pro Thr Leu Gly Phe Ser Thr Pro Gly
        275                 280                 285

Phe Ser Ser Pro Val Ser Ser Thr Pro Ile Ser Pro Ile Phe Gly Pro
        290                 295                 300

Ser Asn Trp His Phe Met Pro Pro Val Ser Glu Val Val Pro Thr Gln
305                 310                 315                 320

Gly Ala Asp Pro Leu Leu Tyr Glu Ser Leu Cys Ser Val Pro Ala Pro
                325                 330                 335

Thr Ser Val Gln Lys Trp Glu Asp Ser Ala His Pro Gln Arg Pro Asp
            340                 345                 350

Asn Ala Asp Leu Ala Ile Leu Tyr Ala Val Val Asp Gly Val Pro Pro
            355                 360                 365

Ala Arg Trp Lys Glu Phe Met Arg Phe Met Gly Leu Ser Glu His Glu
370                 375                 380

Ile Glu Arg Leu Glu Met Gln Asn Gly Arg Cys Leu Arg Glu Ala Gln
385                 390                 395                 400

Tyr Ser Met Leu Glu Ala Trp Arg Arg Arg Thr Pro Arg His Glu Asp
                405                 410                 415

Thr Leu Glu Val Val Gly Leu Val Leu Ser Lys Met Asn Leu Ala Gly
            420                 425                 430

Cys Leu Glu Asn Ile Leu Glu Ala Leu Arg Asn Pro Ala Pro Ser Ser
            435                 440                 445

Thr Thr Arg Leu Pro Arg
450
```